US012697472B2

(12) United States Patent
McCaffrey et al.

(10) Patent No.: US 12,697,472 B2
(45) Date of Patent: Aug. 4, 2026

(54) DRUG DELIVERY DEVICE INCLUDING PUMP WITH FLOATING MICRONEEDLE ASSEMBLY

(71) Applicant: Insulet Corporation, Acton, MA (US)

(72) Inventors: Maureen McCaffrey, Arlington, MA (US); Steven Cardinali, Tewksbury, MA (US); Jason O'Connor, Acton, MA (US)

(73) Assignee: INSULET CORPORATION, Acton, MA (US)

( * ) Notice: Subject to any disclaimer, the term of this patent is extended or adjusted under 35 U.S.C. 154(b) by 1137 days.

(21) Appl. No.: 17/669,106

(22) Filed: Feb. 10, 2022

(65) Prior Publication Data
US 2022/0273927 A1     Sep. 1, 2022

Related U.S. Application Data

(60) Provisional application No. 63/154,003, filed on Feb. 26, 2021.

(51) Int. Cl.
*A61M 37/00* (2006.01)
*A61M 5/142* (2006.01)

(52) U.S. Cl.
CPC .... *A61M 37/0015* (2013.01); *A61M 5/14248* (2013.01); *A61M 2005/14252* (2013.01); *A61M 2037/0023* (2013.01); *A61M 2037/003* (2013.01)

(58) Field of Classification Search
CPC ...... A61M 2037/0061; A61M 37/0015; A61M 2037/0023; A61M 5/14248; A61M 2005/14252; A61M 2005/1585
See application file for complete search history.

(56) References Cited

U.S. PATENT DOCUMENTS

| | | | |
|---|---|---|---|
| 2,667,986 A | 2/1954 | Perelson | |
| 3,631,847 A | 1/1972 | Hobbs | |
| 3,792,703 A | 2/1974 | Moorehead | |
| 3,812,843 A | 5/1974 | Wootten et al. | |

(Continued)

FOREIGN PATENT DOCUMENTS

| | | | |
|---|---|---|---|
| DE | 420595 C | 10/1925 | |
| DE | 19723648 C1 | 8/1998 | |

(Continued)

OTHER PUBLICATIONS

US 5,954,699 A, 09/1999, Jost et al. (withdrawn)

(Continued)

*Primary Examiner* — James D Ponton
(74) *Attorney, Agent, or Firm* — Goodwin Procter LLP

(57) ABSTRACT

Embodiments of the present disclosure relate to techniques, processes, devices or systems including a floating microneedle assembly decoupled from the device and protected by a pump housing. In one approach, a wearable drug delivery device may include a pump housing including a base attachable to a user, and a microneedle assembly coupled to a cannula. The microneedle assembly may be operable to deliver a liquid drug to the user, wherein the microneedle assembly comprises a carrier positioned proximate an opening of the base, and wherein the carrier comprises a plurality of microneedles operable to extend through the opening of the base to penetrate a skin of the user.

7 Claims, 13 Drawing Sheets

(56) References Cited

U.S. PATENT DOCUMENTS

| | | |
|---|---|---|
| 3,841,328 A | 10/1974 | Jensen |
| 3,885,662 A | 5/1975 | Schaefer |
| 4,067,000 A | 1/1978 | Carlson |
| 4,108,177 A | 8/1978 | Pistor |
| 4,151,845 A | 5/1979 | Clemens |
| 4,152,098 A | 5/1979 | Moody et al. |
| 4,193,397 A | 3/1980 | Tucker et al. |
| 4,211,998 A | 7/1980 | Junginger et al. |
| 4,231,019 A | 10/1980 | Junginger et al. |
| 4,261,388 A | 4/1981 | Shelton |
| 4,276,170 A | 6/1981 | Vaillancourt |
| 4,342,311 A | 8/1982 | Whitney et al. |
| 4,364,385 A | 12/1982 | Lossef |
| 4,373,527 A | 2/1983 | Fischell |
| 4,424,720 A | 1/1984 | Bucchianeri |
| 4,435,173 A | 3/1984 | Siposs et al. |
| 4,469,481 A | 9/1984 | Kobayashi |
| 4,475,901 A | 10/1984 | Kraegen et al. |
| 4,498,843 A | 2/1985 | Schneider et al. |
| 4,507,115 A | 3/1985 | Kambara et al. |
| 4,514,732 A | 4/1985 | Hayes, Jr. |
| 4,529,401 A | 7/1985 | Leslie et al. |
| 4,551,134 A | 11/1985 | Slavik et al. |
| 4,559,033 A | 12/1985 | Stephen et al. |
| 4,559,037 A | 12/1985 | Franetzki et al. |
| 4,560,979 A | 12/1985 | Rosskopf |
| 4,562,751 A | 1/1986 | Nason et al. |
| 4,585,439 A | 4/1986 | Michel |
| 4,601,707 A | 7/1986 | Albisser et al. |
| 4,624,661 A | 11/1986 | Arimond |
| 4,634,427 A | 1/1987 | Hannula et al. |
| 4,678,408 A | 7/1987 | Nason et al. |
| 4,684,368 A | 8/1987 | Kenyon |
| 4,685,903 A | 8/1987 | Cable et al. |
| 4,734,092 A | 3/1988 | Millerd |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,801,957 A | 1/1989 | Vandemoere |
| 4,808,161 A | 2/1989 | Kamen |
| 4,836,752 A | 6/1989 | Burkett |
| 4,855,746 A | 8/1989 | Stacy |
| 4,858,619 A | 8/1989 | Toth |
| 4,871,351 A | 10/1989 | Feingold |
| 4,882,600 A | 11/1989 | Van de Moere |
| 4,886,499 A | 12/1989 | Cirelli et al. |
| 4,898,578 A | 2/1990 | Rubalcaba, Jr. |
| 4,898,579 A | 2/1990 | Groshong et al. |
| 4,944,659 A | 7/1990 | Labbe et al. |
| 4,969,874 A | 11/1990 | Michel et al. |
| 4,973,998 A | 11/1990 | Gates |
| 4,985,016 A | 1/1991 | Theeuwes et al. |
| 4,994,047 A | 2/1991 | Walker et al. |
| 5,007,458 A | 4/1991 | Marcus et al. |
| 5,045,871 A | 9/1991 | Reinholdson |
| 5,062,841 A | 11/1991 | Siegel |
| 5,109,850 A | 5/1992 | Blanco et al. |
| 5,125,415 A | 6/1992 | Bell |
| 5,176,662 A | 1/1993 | Bartholomew et al. |
| 5,178,609 A | 1/1993 | Ishikawa |
| 5,189,609 A | 2/1993 | Tivig et al. |
| 5,205,819 A | 4/1993 | Ross et al. |
| 5,213,483 A | 5/1993 | Flaherty et al. |
| 5,232,439 A | 8/1993 | Campbell et al. |
| 5,239,326 A | 8/1993 | Takai |
| 5,244,463 A | 9/1993 | Cordner, Jr. et al. |
| 5,245,447 A | 9/1993 | Stemmle |
| 5,254,096 A | 10/1993 | Rondelet et al. |
| 5,257,980 A | 11/1993 | Van Antwerp et al. |
| 5,261,884 A | 11/1993 | Stern et al. |
| 5,281,202 A | 1/1994 | Weber et al. |
| 5,308,335 A | 5/1994 | Ross et al. |
| 5,312,337 A | 5/1994 | Flaherty et al. |
| 5,318,540 A | 6/1994 | Athayde et al. |
| 5,342,313 A | 8/1994 | Campbell et al. |
| 5,346,476 A | 9/1994 | Elson |
| 5,364,342 A | 11/1994 | Beuchat et al. |
| 5,411,480 A | 5/1995 | Kriesel |
| 5,433,710 A | 7/1995 | VanAntwerp et al. |
| 5,452,033 A | 9/1995 | Balling et al. |
| 5,492,534 A | 2/1996 | Athayde et al. |
| 5,503,628 A | 4/1996 | Fetters et al. |
| 5,505,709 A | 4/1996 | Funderburk et al. |
| 5,507,288 A | 4/1996 | Bocker et al. |
| 5,514,096 A | 5/1996 | Jiejima |
| 5,533,389 A | 7/1996 | Kamen et al. |
| 5,545,152 A | 8/1996 | Funderburk et al. |
| 5,573,342 A | 11/1996 | Patalano |
| 5,575,770 A | 11/1996 | Melsky et al. |
| 5,576,781 A | 11/1996 | Deleeuw |
| 5,582,593 A | 12/1996 | Hultman |
| 5,584,813 A | 12/1996 | Livingston et al. |
| 5,613,956 A | 3/1997 | Patterson et al. |
| 5,630,710 A | 5/1997 | Tune et al. |
| 5,637,095 A | 6/1997 | Nason et al. |
| 5,643,213 A | 7/1997 | McPhee |
| 5,647,853 A | 7/1997 | Feldmann et al. |
| 5,665,065 A | 9/1997 | Colman et al. |
| 5,665,070 A | 9/1997 | McPhee |
| 5,678,539 A | 10/1997 | Schubert et al. |
| 5,685,859 A | 11/1997 | Kommerup |
| 5,693,018 A | 12/1997 | Kriesel et al. |
| 5,695,490 A | 12/1997 | Flaherty et al. |
| 5,702,363 A | 12/1997 | Flaherty |
| 5,704,520 A | 1/1998 | Gross |
| 5,716,343 A | 2/1998 | Kriesel et al. |
| 5,726,404 A | 3/1998 | Brody |
| 5,726,751 A | 3/1998 | Altendorf et al. |
| 5,741,228 A | 4/1998 | Lambrecht et al. |
| 5,747,350 A | 5/1998 | Sattler |
| 5,748,827 A | 5/1998 | Holl et al. |
| 5,755,682 A | 5/1998 | Knudson et al. |
| 5,764,159 A | 6/1998 | Neftel |
| 5,776,103 A | 7/1998 | Kriesel et al. |
| 5,779,676 A | 7/1998 | Kriesel et al. |
| 5,785,681 A | 7/1998 | Indravudh |
| 5,785,688 A | 7/1998 | Joshi et al. |
| 5,797,881 A | 8/1998 | Gadot |
| 5,800,397 A | 9/1998 | Wilson et al. |
| 5,800,405 A | 9/1998 | McPhee |
| 5,800,420 A | 9/1998 | Gross et al. |
| 5,810,015 A | 9/1998 | Flaherty |
| 5,814,020 A | 9/1998 | Gross |
| 5,840,063 A | 11/1998 | Flaherty |
| 5,845,218 A | 12/1998 | Altschul |
| 5,848,990 A | 12/1998 | Cirelli et al. |
| 5,848,991 A | 12/1998 | Gross et al. |
| 5,851,197 A | 12/1998 | Marano et al. |
| 5,858,005 A | 1/1999 | Kriesel |
| 5,858,239 A | 1/1999 | Kenley et al. |
| D405,524 S | 2/1999 | Falk |
| 5,865,806 A | 2/1999 | Howell |
| 5,871,470 A | 2/1999 | McWha |
| 5,875,393 A | 2/1999 | Altschul et al. |
| 5,885,659 A | 3/1999 | Takahashi et al. |
| 5,885,808 A | 3/1999 | Spooner et al. |
| 5,886,647 A | 3/1999 | Badger et al. |
| 5,891,097 A | 4/1999 | Saito et al. |
| 5,897,530 A | 4/1999 | Jackson |
| 5,906,597 A | 5/1999 | McPhee |
| 5,911,716 A | 6/1999 | Rake et al. |
| 5,919,167 A | 7/1999 | Mulhauser et al. |
| 5,921,419 A | 7/1999 | Niedospial, Jr. et al. |
| 5,931,814 A | 8/1999 | Alex et al. |
| 5,935,099 A | 8/1999 | Peterson et al. |
| 5,954,058 A | 9/1999 | Flaherty |
| 5,954,694 A | 9/1999 | Sunseri |
| 5,957,890 A | 9/1999 | Mann et al. |
| 5,957,895 A | 9/1999 | Sage et al. |
| 5,961,492 A | 10/1999 | Kriesel et al. |
| 5,965,848 A | 10/1999 | Altschul et al. |
| 5,983,094 A | 11/1999 | Altschul et al. |
| 5,993,423 A | 11/1999 | Choi |

(56)		References Cited

U.S. PATENT DOCUMENTS

| | | | |
|---|---|---|---|
| 5,997,501 | A | 12/1999 | Gross et al. |
| 6,019,747 | A | 2/2000 | McPhee |
| 6,024,539 | A | 2/2000 | Blomquist |
| 6,050,978 | A | 4/2000 | Orr et al. |
| 6,071,292 | A | 6/2000 | Makower et al. |
| 6,090,080 | A | 7/2000 | Jost et al. |
| 6,090,092 | A | 7/2000 | Fowles et al. |
| 6,126,637 | A | 10/2000 | Kriesel et al. |
| 6,144,847 | A | 11/2000 | Altschul et al. |
| 6,152,898 | A | 11/2000 | Olsen |
| 6,174,300 | B1 | 1/2001 | Kriesel et al. |
| 6,190,359 | B1 | 2/2001 | Heruth |
| 6,200,338 | B1 | 3/2001 | Solomon et al. |
| 6,206,850 | B1 | 3/2001 | Neil |
| 6,244,778 | B1 | 6/2001 | Chesbrough |
| 6,309,370 | B1 | 10/2001 | Haim et al. |
| 6,363,609 | B1 | 4/2002 | Pickren |
| 6,375,638 | B2 | 4/2002 | Nason et al. |
| 6,375,639 | B1 | 4/2002 | Duplessie et al. |
| 6,475,196 | B1 | 11/2002 | Vachon |
| 6,520,936 | B1 | 2/2003 | Mann |
| 6,527,744 | B1 | 3/2003 | Kriesel et al. |
| 6,569,125 | B2 | 5/2003 | Jepson et al. |
| 6,572,542 | B1 | 6/2003 | Houben et al. |
| 6,572,585 | B2 | 6/2003 | Choi |
| 6,666,852 | B2 | 12/2003 | Niedospial, Jr. |
| 6,699,221 | B2 | 3/2004 | Vaillancourt |
| 6,740,059 | B2 | 5/2004 | Flaherty |
| 6,883,778 | B1 | 4/2005 | Newton et al. |
| 7,008,404 | B2 | 3/2006 | Nakajima |
| 7,018,360 | B2 | 3/2006 | Flaherty et al. |
| 7,025,744 | B2 | 4/2006 | Utterberg et al. |
| 7,060,059 | B2 | 6/2006 | Keith et al. |
| 7,128,727 | B2 | 10/2006 | Flaherty et al. |
| 7,144,384 | B2 | 12/2006 | Gorman et al. |
| 7,160,272 | B1 | 1/2007 | Eyal et al. |
| 7,267,665 | B2 | 9/2007 | Steil et al. |
| 7,291,133 | B1 | 11/2007 | Kindler et al. |
| 7,303,549 | B2 | 12/2007 | Flaherty et al. |
| 7,918,825 | B2 | 4/2011 | OConnor et al. |
| 9,402,950 | B2 | 8/2016 | Dilanni et al. |
| 2001/0053895 | A1 | 12/2001 | Vaillancourt |
| 2002/0010423 | A1 | 1/2002 | Gross et al. |
| 2002/0032374 | A1 | 3/2002 | Holker et al. |
| 2002/0066715 | A1 | 6/2002 | Niedospial |
| 2002/0123740 | A1 | 9/2002 | Flaherty et al. |
| 2003/0163097 | A1 | 8/2003 | Fleury et al. |
| 2004/0010207 | A1 | 1/2004 | Flaherty et al. |
| 2004/0064088 | A1 | 4/2004 | Gorman et al. |
| 2004/0088224 | A1 | 5/2004 | Mukai |
| 2004/0092865 | A1 | 5/2004 | Flaherty et al. |
| 2004/0116847 | A1 | 6/2004 | Wall |
| 2004/0158208 | A1 | 8/2004 | Hiejima |
| 2004/0203357 | A1 | 10/2004 | Nassimi |
| 2005/0020980 | A1 | 1/2005 | Inoue et al. |
| 2005/0187524 | A1 | 8/2005 | Willis et al. |
| 2005/0203461 | A1 | 9/2005 | Flaherty et al. |
| 2005/0238507 | A1 | 10/2005 | Dilanni et al. |
| 2005/0258581 | A1 | 11/2005 | Tanaka |
| 2006/0134323 | A1 | 6/2006 | OBrien |
| 2006/0155210 | A1 | 7/2006 | Beckman et al. |
| 2006/0178633 | A1 | 8/2006 | Garibotto et al. |
| 2006/0204535 | A1 | 9/2006 | Johnson |
| 2006/0253085 | A1 | 11/2006 | Geismar et al. |
| 2006/0282290 | A1 | 12/2006 | Flaherty et al. |
| 2007/0005018 | A1 | 1/2007 | Tekbuchava |
| 2007/0025811 | A1 | 2/2007 | Wilhelm |
| 2007/0112332 | A1 | 5/2007 | Harding et al. |
| 2007/0118405 | A1 | 5/2007 | Campbell et al. |
| 2007/0129690 | A1 | 6/2007 | Rosenblatt et al. |
| 2007/0173974 | A1 | 7/2007 | Lin |
| 2007/0197163 | A1 | 8/2007 | Robertson |
| 2007/0282269 | A1 | 12/2007 | Carter et al. |
| 2008/0004515 | A1 | 1/2008 | Jennewine |

| | | | |
|---|---|---|---|
| 2008/0051738 | A1* | 2/2008 | Griffin ................. A61M 5/158 |
| | | | 604/272 |
| 2008/0065000 | A1 | 3/2008 | Bidinger et al. |
| 2008/0065050 | A1 | 3/2008 | Sparks et al. |
| 2008/0078400 | A1 | 4/2008 | Martens et al. |
| 2008/0132880 | A1 | 6/2008 | Buchman |
| 2008/0249508 | A1 | 10/2008 | Lopez et al. |
| 2008/0287906 | A1 | 11/2008 | Burkholz et al. |
| 2009/0054866 | A1 | 2/2009 | Teisen-Simony et al. |
| 2009/0062767 | A1 | 3/2009 | Van Antwerp et al. |
| 2009/0069787 | A1 | 3/2009 | Estes et al. |
| 2009/0099521 | A1 | 4/2009 | Gravesen et al. |
| 2009/0124979 | A1 | 5/2009 | Raymond et al. |
| 2009/0198215 | A1 | 8/2009 | Chong et al. |
| 2009/0299300 | A1 | 12/2009 | Truitt et al. |
| 2010/0137784 | A1 | 6/2010 | Cefai et al. |
| 2010/0152658 | A1 | 6/2010 | Hanson et al. |
| 2011/0054390 | A1 | 3/2011 | Searle et al. |
| 2011/0054399 | A1 | 3/2011 | Chong et al. |
| 2011/0144586 | A1 | 6/2011 | Michaud et al. |
| 2011/0166512 | A1 | 7/2011 | Both et al. |
| 2011/0230833 | A1 | 9/2011 | Landman et al. |
| 2011/0251509 | A1 | 10/2011 | Beyhan et al. |
| 2011/0316562 | A1 | 12/2011 | Cefai et al. |
| 2012/0003093 | A1 | 1/2012 | Lischer et al. |
| 2012/0003935 | A1 | 1/2012 | Lydon et al. |
| 2012/0010594 | A1 | 1/2012 | Holt et al. |
| 2012/0078161 | A1 | 3/2012 | Masterson et al. |
| 2012/0109066 | A1 | 5/2012 | Chase et al. |
| 2012/0238851 | A1 | 9/2012 | Kamen et al. |
| 2012/0277668 | A1 | 11/2012 | Chawla |
| 2013/0060233 | A1 | 3/2013 | OConnor et al. |
| 2013/0178791 | A1 | 7/2013 | Javitt |
| 2013/0317753 | A1 | 11/2013 | Kamen et al. |
| 2014/0074033 | A1 | 3/2014 | Sonderegger et al. |
| 2014/0127048 | A1 | 5/2014 | Dilanni et al. |
| 2014/0128839 | A1 | 5/2014 | Dilanni et al. |
| 2014/0135880 | A1 | 5/2014 | Baumgartner et al. |
| 2014/0316379 | A1 | 10/2014 | Sonderegger et al. |
| 2015/0320990 | A1* | 11/2015 | Burton ................ A61M 5/1454 |
| | | | 604/173 |
| 2016/0015891 | A1 | 1/2016 | Papiorek |
| 2016/0038689 | A1 | 2/2016 | Lee et al. |
| 2016/0302054 | A1 | 10/2016 | Kimura et al. |
| 2017/0128664 | A1 | 5/2017 | Diianni et al. |
| 2019/0160273 | A1 | 5/2019 | Baker et al. |

FOREIGN PATENT DOCUMENTS

| | | |
|---|---|---|
| DE | 19920896 A1 | 11/2000 |
| EP | 0341049 A2 | 11/1989 |
| EP | 342947 A2 | 11/1989 |
| EP | 0496305 A2 | 7/1992 |
| EP | 0763369 A1 | 3/1997 |
| EP | 0867196 A2 | 9/1998 |
| EP | 0937475 A2 | 8/1999 |
| EP | 2397181 A1 | 12/2011 |
| EP | 2830499 A1 | 2/2015 |
| GB | 875034 A | 8/1961 |
| GB | 2443261 A | 4/2008 |
| TW | 200740148 A | 10/2007 |
| TW | M452390 U | 5/2013 |
| WO | 8101658 A1 | 6/1981 |
| WO | 8606796 A1 | 11/1986 |
| WO | 9800193 A1 | 1/1998 |
| WO | 9801071 A1 | 1/1998 |
| WO | 9856293 A1 | 12/1998 |
| WO | 9910040 A1 | 3/1999 |
| WO | 9956803 A1 | 11/1999 |
| WO | 9962576 A1 | 12/1999 |
| WO | 0019887 A1 | 4/2000 |
| WO | 0029047 A1 | 5/2000 |
| WO | 0029049 A1 | 5/2000 |
| WO | 0030705 A1 | 6/2000 |
| WO | 0061215 A1 | 10/2000 |
| WO | 0074752 A1 | 12/2000 |
| WO | 0078210 A1 | 12/2000 |
| WO | 0152727 A1 | 7/2001 |
| WO | 0156633 A2 | 8/2001 |

(56)           References Cited

FOREIGN PATENT DOCUMENTS

| WO | 0176684 | A1 | 10/2001 |
| WO | 0220073 | A2 | 3/2002 |
| WO | 0226282 | A2 | 4/2002 |
| WO | 0240083 | A2 | 5/2002 |
| WO | 2002068823 | | 9/2002 |
| WO | 2003030984 | A1 | 4/2003 |
| WO | 03090509 | A2 | 11/2003 |
| WO | 200172354 | A2 | 11/2003 |
| WO | 2002015954 | A1 | 11/2003 |
| WO | 2006053007 | A2 | 5/2006 |
| WO | 2007064835 | A2 | 6/2007 |
| WO | 2008024810 | A2 | 2/2008 |
| WO | 2008133702 | A1 | 11/2008 |
| WO | 2009098648 | A2 | 8/2009 |
| WO | 2011095483 | A1 | 8/2011 |
| WO | 2012045667 | A2 | 4/2012 |
| WO | 2012108959 | A1 | 8/2012 |
| WO | 2012134588 | A1 | 10/2012 |
| WO | 2012134589 | A1 | 10/2012 |
| WO | 2013078200 | A1 | 5/2013 |
| WO | 2013134486 | A2 | 9/2013 |
| WO | 2013149186 | A1 | 10/2013 |
| WO | 2013182321 | A1 | 12/2013 |
| WO | 2014099404 | A1 | 6/2014 |
| WO | 2014194183 | A2 | 12/2014 |
| WO | 2015061493 | A1 | 4/2015 |
| WO | 2015081337 | A2 | 6/2015 |
| WO | 2016141082 | A1 | 9/2016 |
| WO | 2017205816 | A1 | 11/2017 |

OTHER PUBLICATIONS

International Search Report and Written Opinion for PCT Application No. PCT/US2018/018901, dated Aug. 6, 2018, 12 pages.

International Search Report and Written Opinion for PCT Application No. PCT/US2017/015601, mailed on May 16, 2017, 12 pages.

International Search Report and Written Opinion for PCT Application No. PCT/US18/52464, mailed on Jan. 4, 2019, 11 pages.

International Preliminary Report on Patentability mailed on Oct. 9, 2014, issued in PCT Patent Application No. PCT/US2013/034674, 14 pages.

International Search Report and Written Opinion for PCT Application No. PCT/US2022/015985, mailed May 30, 2022, 13 pages.

International Preliminary Report on Patentability mailed on Apr. 9, 2020, issued in PCT Patent Application No. PCT/US2018/052464, 7 pages.

Web-Site Brochure dated Jan. 4, 2000. MiniMed 508. "Doing its job. Naturally." www.minimed.com/files/mm113.htm.

Web-Site Brochure dated Jan. 4, 2000. SOOIL—Homepage. "Portable Insulin Pump".www.sooil.com/intro2.htm.

Web-Site Brochure dated Dec. 20, 1999. "The Animas R-1000 Insulin Pump". www.animascorp.com/pump_f_s.html.

Web-Site Brochure dated Jan. 4, 2000. SOOIL—Homepage. "Portable Insulin Pump". www.sooil.com/product2.htm.

Web-Site Brochure dated Jan. 4, 2000. SOOIL—Homepage. "Portable Insulin Pump".www.sooil.com/product3.htm.

Web-Site Brochure dated Jan. 4, 2000. SOOIL—Homepage. "Portable Insulin Pump". www.sooil.com/product4.htm.

EPO Search Report dated Nov. 11, 2015, received in corresponding Application No. 13768938.6, 7 pgs.

International Search Report and Written Opinion for PCT Application No. PCT/GB2015/050248, mailed Jun. 23, 2015, 11 pages.

Web-Site Brochure dated Jan. 4, 2000. "The Glucose Sensor".www.animascorp.corn/sensor_f.html.

Web-Site Brochure dated Dec. 20, 1999. Applied Medical Technology.—"508 Pump Information". www.applied-medical.co.uk/508.htm.

User's Guide for Model 508 Insulin Pump, Mini Med, 8/00, 153 pages.

International Search Report for PCT Application No. PCT/US03/16640, dated Oct. 2, 2003, 1 page.

* cited by examiner

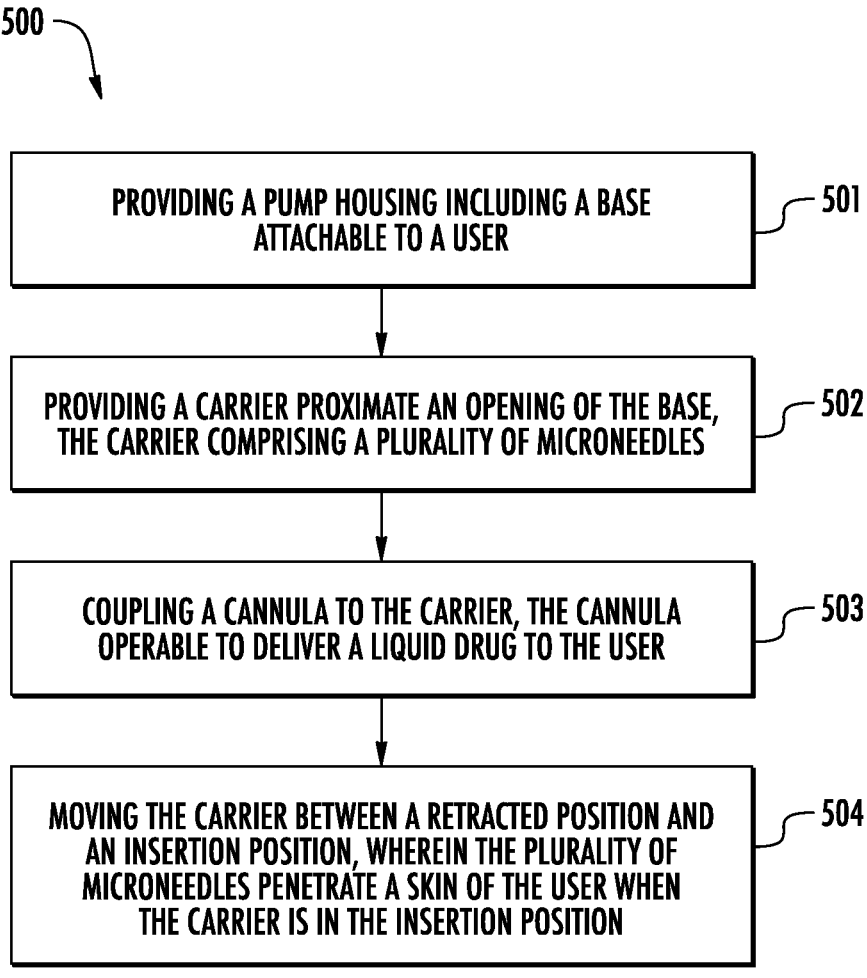

500

PROVIDING A PUMP HOUSING INCLUDING A BASE ATTACHABLE TO A USER — 501

PROVIDING A CARRIER PROXIMATE AN OPENING OF THE BASE, THE CARRIER COMPRISING A PLURALITY OF MICRONEEDLES — 502

COUPLING A CANNULA TO THE CARRIER, THE CANNULA OPERABLE TO DELIVER A LIQUID DRUG TO THE USER — 503

MOVING THE CARRIER BETWEEN A RETRACTED POSITION AND AN INSERTION POSITION, WHEREIN THE PLURALITY OF MICRONEEDLES PENETRATE A SKIN OF THE USER WHEN THE CARRIER IS IN THE INSERTION POSITION — 504

FIG. 6

DRUG DELIVERY DEVICE INCLUDING PUMP WITH FLOATING MICRONEEDLE ASSEMBLY

CROSS REFERENCE TO RELATED APPLICATIONS

This application claims the benefit of U.S. Provisional Application Ser. No. 63/154,003, filed Feb. 26, 2021, the teachings of which are incorporated herein by reference.

TECHNICAL FIELD

The disclosed embodiments generally relate to medication delivery. More particularly, the disclosed embodiments relate to techniques, processes, systems, and pump devices including a floating microneedle assembly.

BACKGROUND

A user may wear a medical device on his or her body for any of a variety of reasons, such as medication injection, heart rate monitoring, glucose monitoring, etc. Many wearable medication delivery devices use a cannula and injectable subcutaneous needle to deliver a liquid drug to the user. Some devices include a microneedle array to deliver the liquid drug, as microneedles have been found to increase pharmacokinetics and to decrease pain as compared to subcutaneous needles. Microneedles are inserted into the dermal layer of the skin but typically do not reach the subcutaneous layer. Because wearable devices are likely to get bumped, leaned on, caught on clothing, etc., it is more likely the microneedles may be pulled from of the skin of the user, ultimately causing the patient to receive an improper drug dose.

Accordingly, improved approaches for securing a microneedle array of a drug delivery device to a user are needed.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In some approaches, a wearable drug delivery device may include a pump housing including a base attachable to a user, and a microneedle assembly coupled to a cannula. The microneedle assembly may be operable to deliver a liquid drug to the user, wherein the microneedle assembly comprises a carrier positioned proximate an opening of the base, and wherein the carrier comprises a plurality of microneedles operable to extend through the opening of the base to penetrate a skin of the user.

In some approaches, a microneedle assembly of a wearable drug delivery device may include a carrier coupled to a cannula, a microneedle housing surrounding the carrier, wherein the microneedle and the carrier are decoupled from one another, and a plurality of microneedles extending from the carrier. The plurality of microneedles may be operable to receive a liquid drug from the cannula and penetrate a skin of the user to deliver the liquid drug to the user when the carrier is biased relative to the microneedle housing.

Furthermore, in some approaches, a method of operating a microneedle assembly of a wearable drug delivery device may include providing a pump housing including a base attachable to a user, and providing a carrier proximate an opening of the base, the carrier comprising a plurality of microneedles. The method may further include coupling a cannula to the carrier, the cannula operable to deliver a liquid drug to the user, and moving the carrier between a retracted position and an insertion position, wherein the plurality of microneedles penetrate a skin of the user when the carrier is in the insertion position.

BRIEF DESCRIPTION OF THE DRAWINGS

In the drawings, like reference characters generally refer to the same parts throughout the different views. In the following description, various embodiments of the present disclosure are described with reference to the following drawings, in which:

FIG. 6 illustrates a process flow of a method according to embodiments of the present disclosure.

Figure 1A:
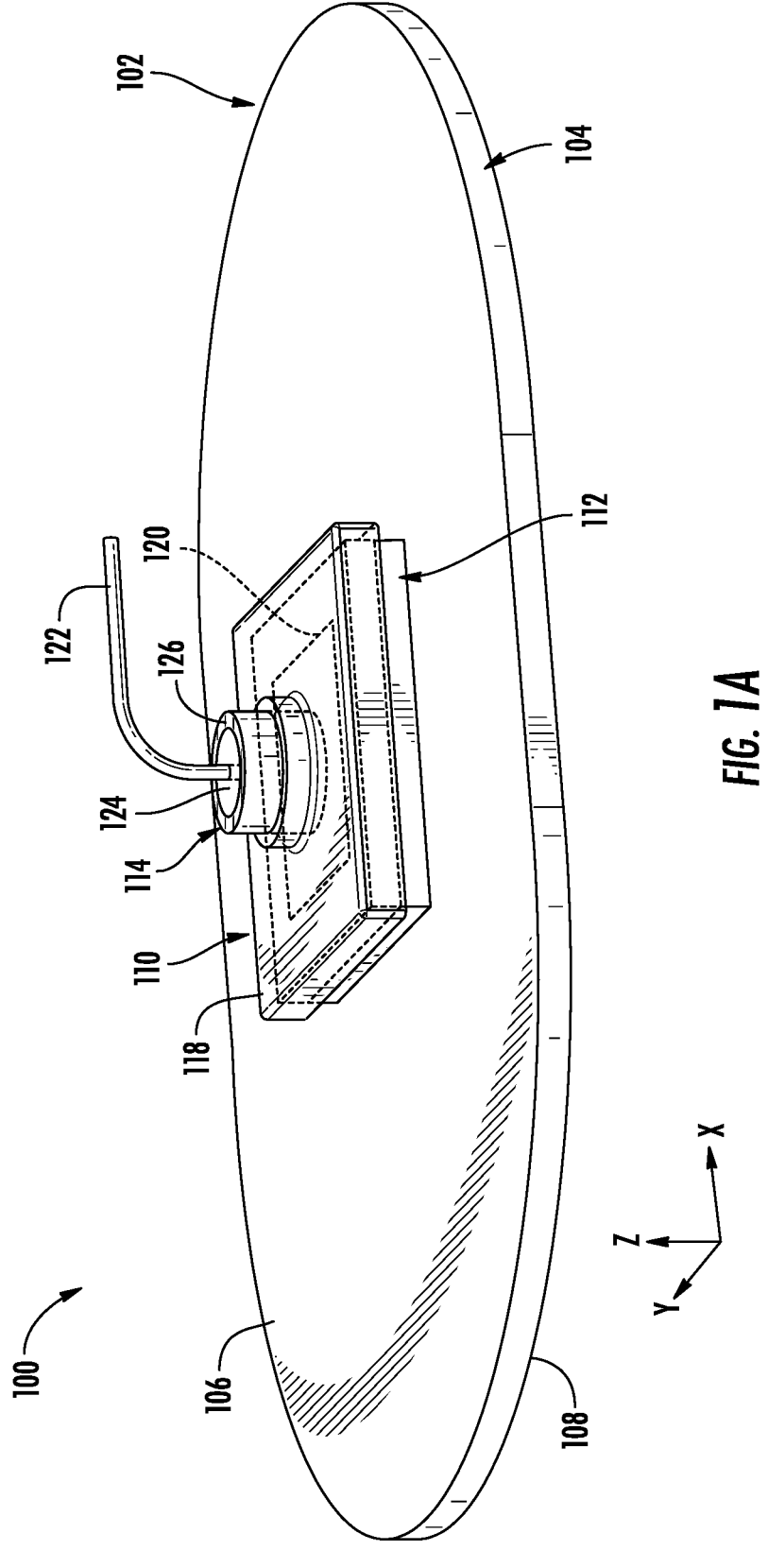
FIG. 1A is a perspective view of a wearable drug delivery device according to embodiments of the present disclosure.

The drawings are not necessarily to scale. The drawings are merely representations, not intended to portray specific parameters of the disclosure. The drawings are intended to depict exemplary embodiments of the disclosure, and therefore are not be considered as limiting in scope. Furthermore, certain elements in some of the figures may be omitted, or illustrated not-to-scale, for illustrative clarity. Still furthermore, for clarity, some reference numbers may be omitted in certain drawings.

DETAILED DESCRIPTION

Systems, devices, and methods in accordance with the present disclosure will now be described more fully hereinafter with reference to the accompanying drawings, where one or more embodiments are shown. The systems, devices, and methods may be embodied in many different forms and are not to be construed as being limited to the embodiments set forth herein. Instead, these embodiments are provided so the disclosure will be thorough and complete, and will fully convey the scope of methods and devices to those skilled in the art. Each of the systems, devices, and methods disclosed herein provides one or more advantages over conventional systems, components, and methods.

Embodiments of the present disclosure provide a wearable drug delivery device including a microneedle assembly decoupled from the wearable drug delivery device and protected by a pump housing and a pump body. The wearable drug delivery device may include an analyte sensor, such as a blood glucose sensor, and the microneedle assembly may be operable in allowing the device to measure an analyte level in a user of the device. As noted above, the shallow insertion depth of the microneedles means there is a higher risk of the microneedles coming out of the skin as compared with a subcutaneous needle or catheter. To address the deficiencies of the current art, embodiments herein provide a microneedle housing operable to constrain a carrier containing the microneedles only in the positive z-axis (e.g., away from the skin). As a result, lateral and upward forces on the pump housing are less likely to transfer to the microneedles. By decoupling the pump housing from the microneedle assembly, the carrier and microneedles are not subject to the same contact forces as the pump body, which decreases the risk that the microneedles will come out of the skin when a force is imparted on the pump body.

In some embodiments, the microneedle assembly is connected to a fluid path inside the pump. For example, the carrier may include an inlet and internal cavity operable to receive a liquid drug from a cannula. The cannula may include a first end terminating within the internal cavity, and a second end fluidly connected with a reservoir of the wearable drug delivery device.

In some embodiments, the wearable drug delivery device may include one or more layers of adhesive. For example, an adhesive may be attached to an outer side of the carrier and/or a base of the pump housing. Providing the adhesive along the carrier may further secure the carrier to the skin of the user.

In some embodiments, the microneedle assembly may include one or more biasing devices operable to force the carrier and microneedles towards the user. For example, a spring (e.g., torsion spring) may include one or more free ends in contact with the carrier in a deflected configuration. As the spring transitions from the deflected configuration to a relaxed or natural position, the free ends exert a force on the carrier, causing the microneedles to engage the skin of the user. In another example, the spring may engage a cam or sloped surface of the carrier, allowing the carrier to be biased towards the user as the spring rotates.

In some embodiments, the microneedles may be integrally formed with the base of the pump housing. Although non-limiting, the base and microneedles may be molded in a biocompatible polymer, such as Poly(methyl methacrylate). The number and size of the microneedles can be designed such that the total cross sectional area of the microneedle holes meets flow rate needs for delivering a proper dose of the liquid drug to the user.

In some embodiments, the microneedle assembly may be manually inserted, which allows for a significant reduction of both size and part count since there is no need for an insertion mechanism inside the wearable drug delivery device. In turn, the overall size of the wearable drug delivery device may be reduced, which is less burdensome for users.

Figure 1B:
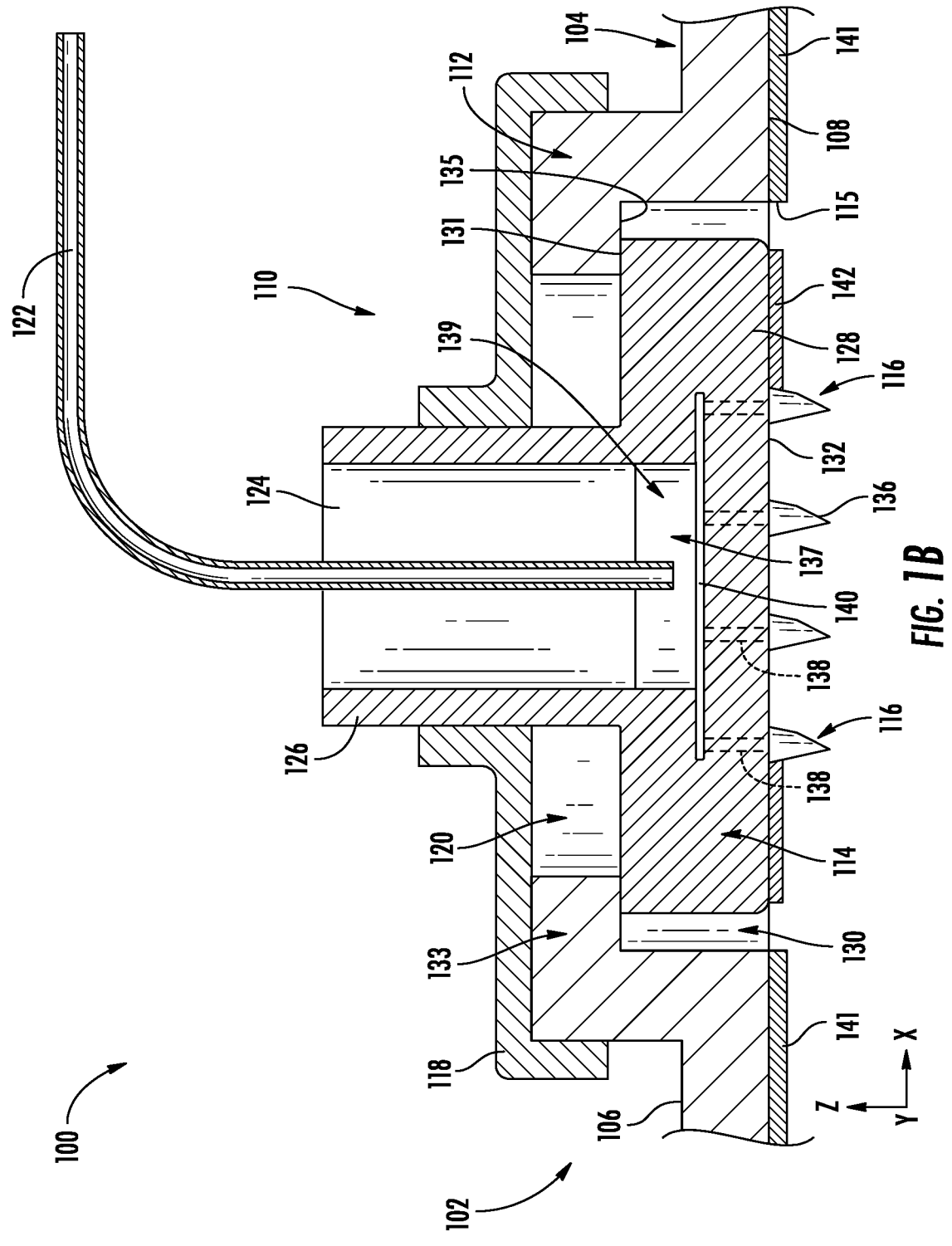
FIG. 1B is a side cross-sectional view of the wearable drug delivery device of FIG. 1A according to embodiments of the present disclosure.

FIGS. 1A-1B illustrate a portion of a device 100 according to embodiments of the present disclosure. The device 100 may be a wearable device such as on-body drug delivery device and/or an analyte sensor. Certain aspects of the device 100 are omitted for brevity and ease of explanation.

As shown, the device 100 may include a pump housing 102 including a base 104 operable to be secured to the skin of a user. The base 104 may include an inner side 106 opposite an outer side 108, wherein the outer side 108 is directly attachable to the user.

The device 100 may further include a microneedle assembly (hereinafter "assembly") 110 connected to the base 104. In some embodiments, the assembly 110 may include a microneedle housing 112 and a carrier 114 positioned within the microneedle housing 112, wherein the carrier 114 includes a plurality of microneedles 116 (FIG. 1B) operable to penetrate the skin of the user to deliver a liquid drug to the user. The microneedle housing 112 may be an integral part of the base 104, as shown, or a separate component coupled to the base 104. In some embodiments, the microneedle housing 112 and the carrier 114 may be covered by a sterile liquid barrier 118, wherein the liquid barrier 118 may extend across a first opening 120 of the microneedle housing 112. Although non-limiting, the liquid barrier 118 may be a polymer or silicon layer operable to provide a liquid tight seal between the liquid barrier 118, the microneedle housing 112, and the carrier 114. As shown, the liquid barrier 118 may be coupled to the microneedle housing 112.

The assembly 110 may be coupled to a cannula 122 of the device 100. As will be described in greater detail herein, the cannula 122 may be connected along a fluid path to a reservoir containing the liquid drug. In some embodiments, the cannula 122 may be secured to the carrier 114 by an o-ring or plug 124 positioned within a neck 126 of the carrier 114.

As best shown in FIG. 1B, the carrier 114 may include a main body 128 connected to the neck 126, wherein the main body 128 is positioned within a recess 130 defined by the microneedle housing 112. The main body 128 includes an inner surface 131 opposite an outer surface 132, wherein the inner surface 131 may engage a retention feature 133 to prevent the carrier 114 from moving away from the user, e.g., along the z-axis. In some embodiments, the retention feature 133 is a flange defining the first opening 120 of the microneedle housing 112, wherein an underside 135 of the flange may abut or contact the inner surface 131 of the carrier 114. In a fully engaged position of the assembly 110, the outer surface 132 of the carrier 114 may be co-planar with the outer side 108 of the base 104.

As shown, the microneedles 116 may extend from the outer surface 132 of the carrier 114. Although non-limiting, the microneedles 116 may be arranged as an array having any number of rows and columns. The microneedles 116 and/or the carrier 114 may be integrally manufactured out of a metal, polymer, or silicon. In various embodiments, the number and size of the microneedles 116 can be designed such that the total cross sectional area of the microneedle holes meets flow rate needs of a patient requiring the liquid drug. In some embodiments, each of the microneedles 116 may include a beveled surface 136 for easier insertion. Embodiments herein are not limited in this context.

During operation, the carrier 114 may be pressed against the skin of the user through an opening 115 of the base 104, causing the microneedles 116 to penetrate the skin. The liquid drug may then be delivered through the cannula 122 and into an internal cavity 137 of the carrier 114. The internal cavity 137 may include a slot 140 connected to a main chamber 139, which may be defined by the inner walls of the neck 126 and a bottom surface of the plug 124. The slot 140 may be fluidly connected with one or more internal fluid conduits 138 of each microneedle 116 for delivering the liquid drug from the main chamber 139 to the dermal layer of the skin.

As further shown, in some embodiments, the device 100 may include a first adhesive 141 along the outer side 108 of the base 104 and a second adhesive 142 along the outer surface 132 of the carrier 114. The first and second adhesives 141, 142 may be adhesive pads or layers attachable to the device 100 and to the skin of the user. In various embodiments, any portion of the outer side 108 of the base 104 can include the first adhesive 141, and any portion of the outer surface 132 of the carrier 114 can include the second adhesive 142. The first and second adhesives 141, 142 may be the same or different in various embodiments. More specifically, the first and second adhesives 141, 142 may be the same or different materials having the same or variable adhesive strengths. In other embodiments, no adhesive is present along the outer side 108 of the base 104 and/or the outer surface 132 of the carrier 114.

The carrier 114 is advantageously decoupled from the microneedle housing 112, allowing the carrier 114 to "float" within the recess 130. As a result, upward forces (e.g., along the z-axis) on the base 104 will not transfer to the carrier 114 or the microneedles 116. Furthermore, due to the width (e.g., along the x-axis) of the first opening 120 and the recess 130, lateral forces (e.g., along the x-axis and y-axis) are less likely to transfer to the carrier 114 or the microneedles 116. In some embodiments, the neck 126 of the carrier 114 and the liquid barrier 118 may slide relative to one another in the event the microneedle housing 112 moves in the z-axis.

Figure 2A:
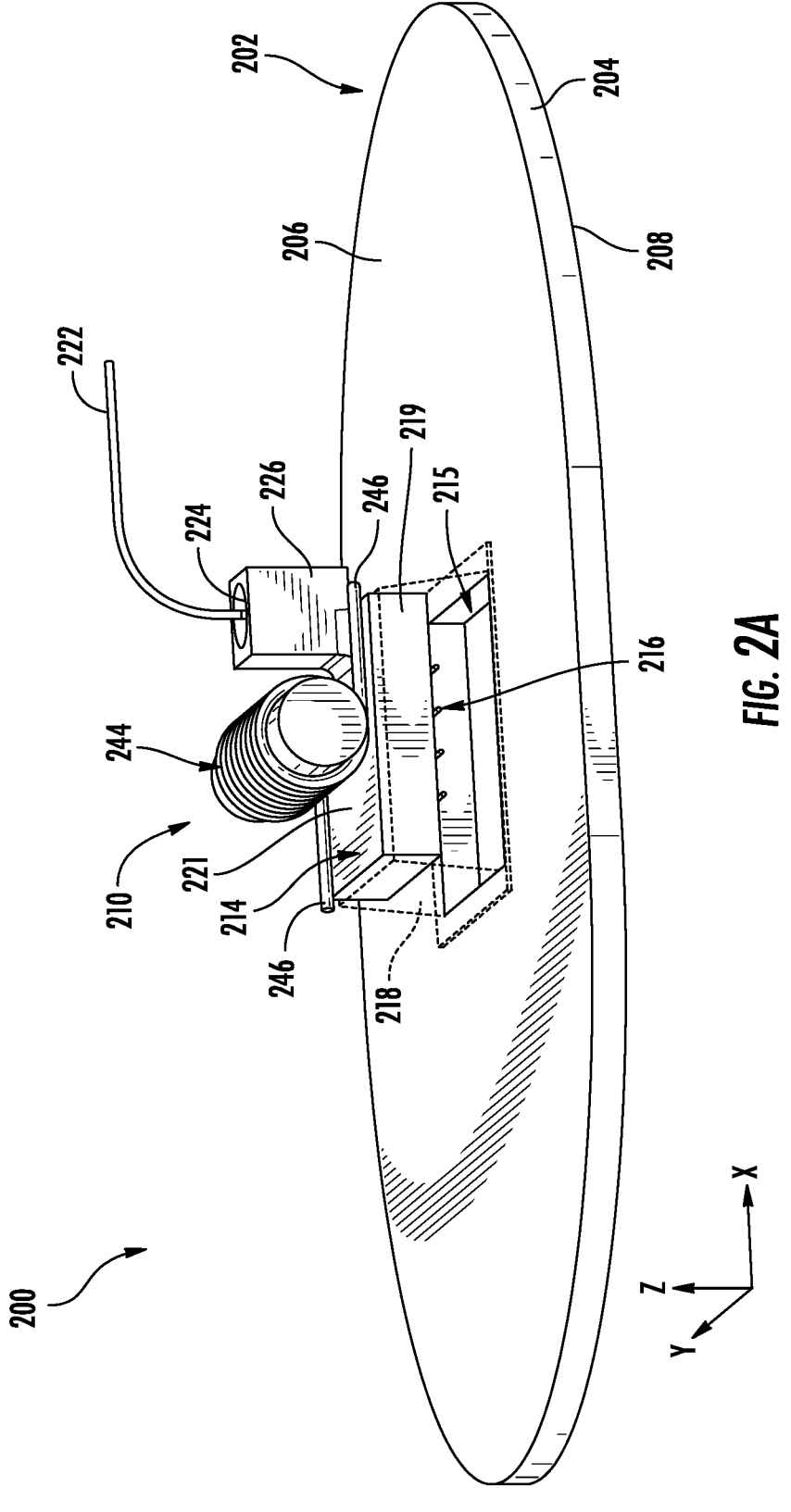
FIG. 2A is a perspective view of a wearable drug delivery device according to embodiments of the present disclosure.
Figure 2B:
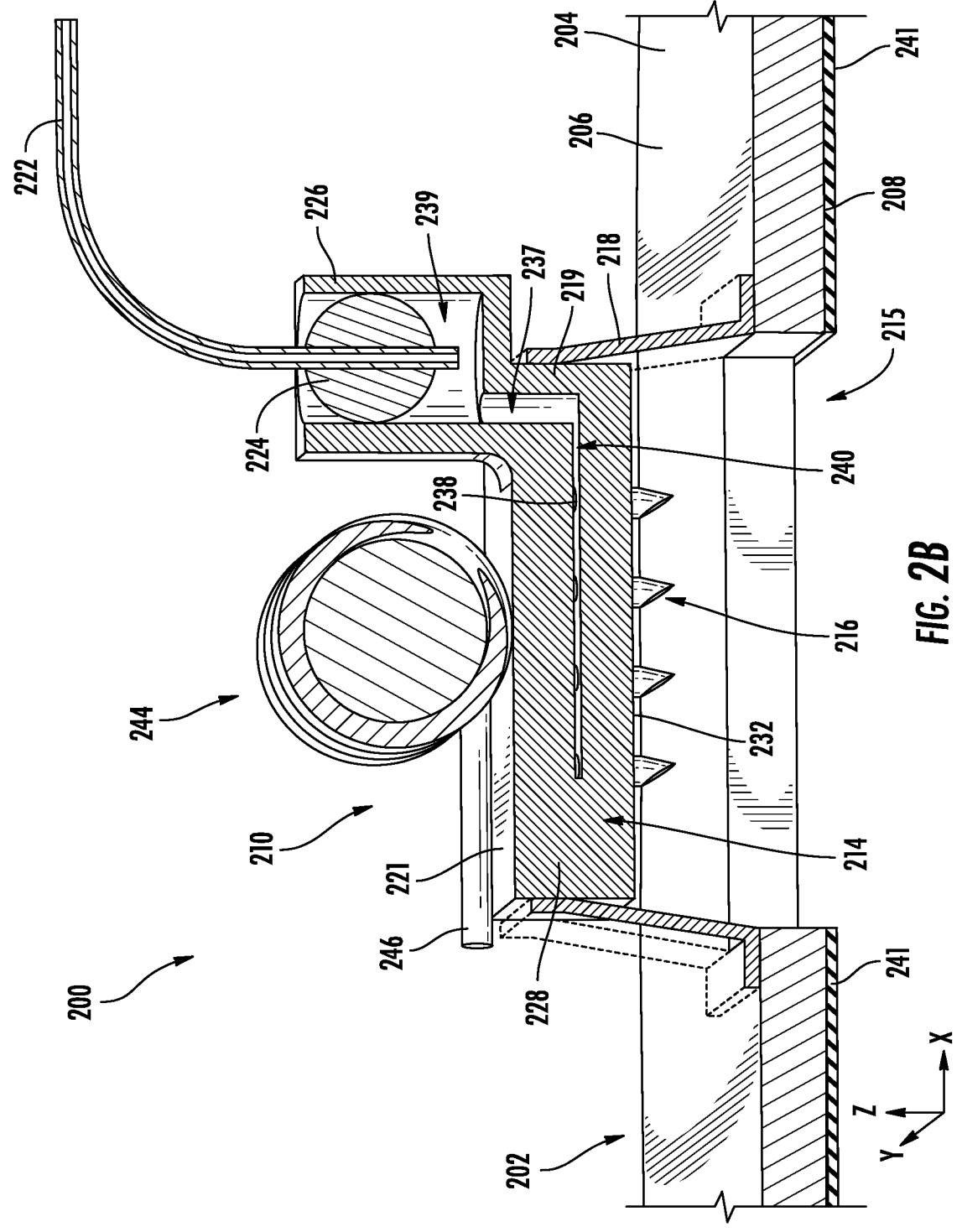
FIG. 2B is a perspective cross-sectional view of the wearable drug delivery device of FIG. 2A according to embodiments of the present disclosure.

FIGS. 2A-2B illustrate a portion of a device 200 according to embodiments of the present disclosure. The device 200 may be a wearable such as an on-body drug delivery device and/or an analyte sensor. Certain aspects of the device 200 are omitted for brevity and ease of explanation. As shown, the device 200 may include a pump housing 202 including a base 204 operable to be secured to the skin of a user. The base 204 may include an inner side 206 opposite an outer side 208, wherein the outer side 208 is directly attachable to the user. As will be described in greater detail below, a carrier 214 may be biased towards the skin of the user by a biasing device 244 operable to move the carrier 214 between a retraction position and an insertion position.

The device 200 may further include a microneedle assembly (hereinafter "assembly") 210 connected to the base 204. In some embodiments, the assembly 210 may include a carrier 214 positioned within a liquid barrier 218. Although shown as attached to side surfaces 219 of the carrier 214, the liquid barrier 218 may extend over a top surface 221 of the carrier 214 in other embodiments. The liquid barrier 218 may be flexible to permit movement of the carrier 214 relative to the base 204 while still maintaining a fluid seal between the carrier 214 and the base 204. As shown, the liquid barrier 218 may be directly secured to the base 204, e.g., along inner side 206 thereof. In other embodiments, the liquid barrier 218 may be secured to the outer side 208 of the base 204, or embedded within the base 204.

The carrier 214 may include a plurality of microneedles 216 operable to penetrate the skin of the user, e.g., through an opening 215 of the base 204, to sample an analyte level or to deliver a liquid drug from a cannula 222 to the user. The cannula 222 may be connected along a fluid path to a reservoir (not shown) containing the liquid drug. In some embodiments, the cannula 222 may be secured to the carrier 214 by an o-ring or plug 224 positioned within a neck 226 of the carrier 214.

As best shown in the cross-sectional view of FIG. 2B, the liquid drug may be delivered through the cannula 222 and into an internal cavity 237 of the carrier 214. The internal cavity 237 may include a slot 240 connected to a main chamber 239 of the neck 226, beneath the plug 224. The slot 240 may be fluidly connected with one or more internal fluid conduits 238 of each microneedle 216 for delivering the liquid drug into the dermal layer of the skin.

In some embodiments, the carrier 214 may further include a main body 228 connected to the neck 226, wherein the main body 228 is positioned above the opening 215 of the base 204. The microneedles 216 may extend from an outer surface 232 of the main body 228, e.g., along the z-axis. Although non-limiting, the microneedles 216 may be arranged as an array having any number of rows and columns. The microneedles 216 and/or the carrier 214 may be integrally manufactured out of a metal, polymer, or silicon. In various embodiments, the number and size of the microneedles 216 can be designed such that the total cross sectional area of the microneedle holes meets flow rate needs of a patient requiring the liquid drug. In some embodiments, each of the microneedles 216 may include a beveled surface 236 for easier insertion into the skin of the user.

In some embodiments, the device 200 may include a first adhesive 241 along the outer side 208 of the base 204 and a second adhesive 242 (FIGS. 3A-3B) along the outer surface 232 of the carrier 214. The first and second adhesives 241, 242 may be adhesive pads or layers attachable to the device 200 and to the skin of the user. In various embodiments, all or any portion of the outer side 208 of the base 204 can include the first adhesive 241, and all or any portion of the outer surface 232 of the carrier 214 can include the second adhesive 242. In other embodiments, no adhesive is present along the outer side 208 of the base 204 and/or the outer surface 232 of the carrier 214.

As shown, the carrier 214 is advantageously decoupled from the housing 202, allowing the carrier 214 to "float" relative to the base 204. As a result, upward forces (e.g., along the z-axis) on the base 204 will not transfer to the carrier 214 or the microneedles 216. Furthermore, due to the width (e.g., along the x-axis) of the opening 215 of the base 204 relative to a width of the carrier 214, lateral forces (e.g., along the x-axis and y-axis) are less likely to transfer to the carrier 214 and thus the microneedles 216.

Figures 3A, 3B:
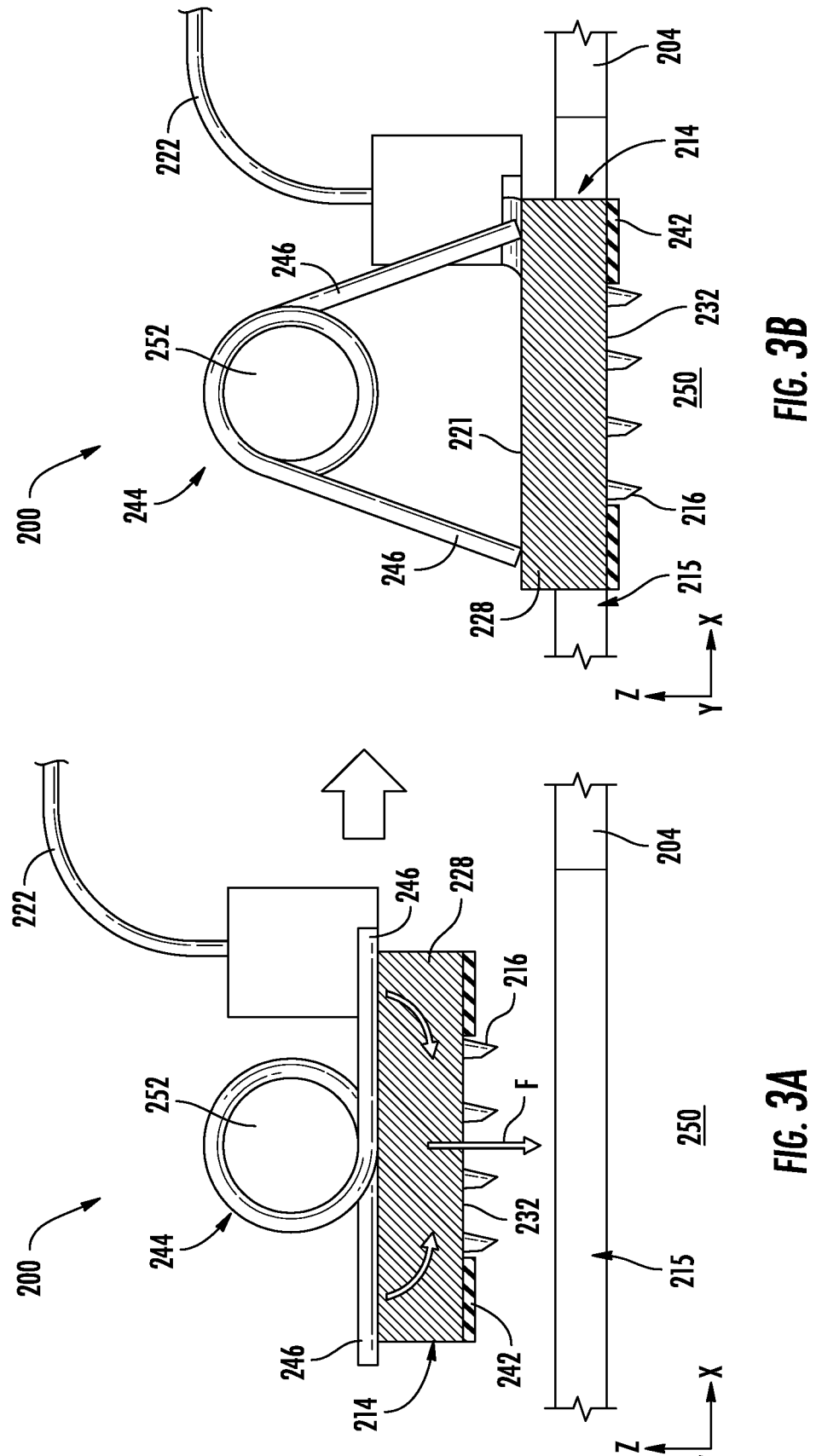
FIGS. 3A-3B demonstrate operation of the wearable drug delivery device of FIGS. 2A-2B according to embodiments of the present disclosure.

Turning to FIGS. 3A-3B, operation of the device 200 will be described in greater detail. As shown, the carrier 214 may be biased from an initial position, as shown in FIG. 3A, to a final insertion position, as shown in FIG. 3B, by a biasing device 244. The insertion can be initiated mechanically or electromechanically. In some embodiments, the biasing device 244 is a coil spring having one or more tines 246 in contact with the top surface 221 of the carrier 214. The tines 246 may rotate about a center support 252, resulting in a downward force 'F' towards a skin 250 of the user. In some embodiments, the tines 246 may be offset from one another along the y-axis and x-axis to ensure the force is provided substantially through a center of carrier 214. Although not shown, in some embodiments, a support or retention member may engage the carrier 214 to initially prevent the carrier 214 from being biased through the opening 215 of the base 204. When desired by the user, the support 252 may be moved or released, which causes the carrier 214 to engage the skin 250 of the user. Once the microneedles 216 penetrate the skin 250, the liquid drug may be delivered through the cannula 222 and the main body 228 of the carrier 214. After application of the carrier 214, the biasing device 244 may provide a sustained force on the microneedles 216 to further decrease the risk of the microneedles 216 coming out of the skin 250. In various embodiments, the force can be optimized by varying properties (e.g., type, shape, thickness, etc.) of the biasing device 244 to maintain a position of the carrier 214 while also avoiding unnecessary patient discomfort.

Figure 4A:
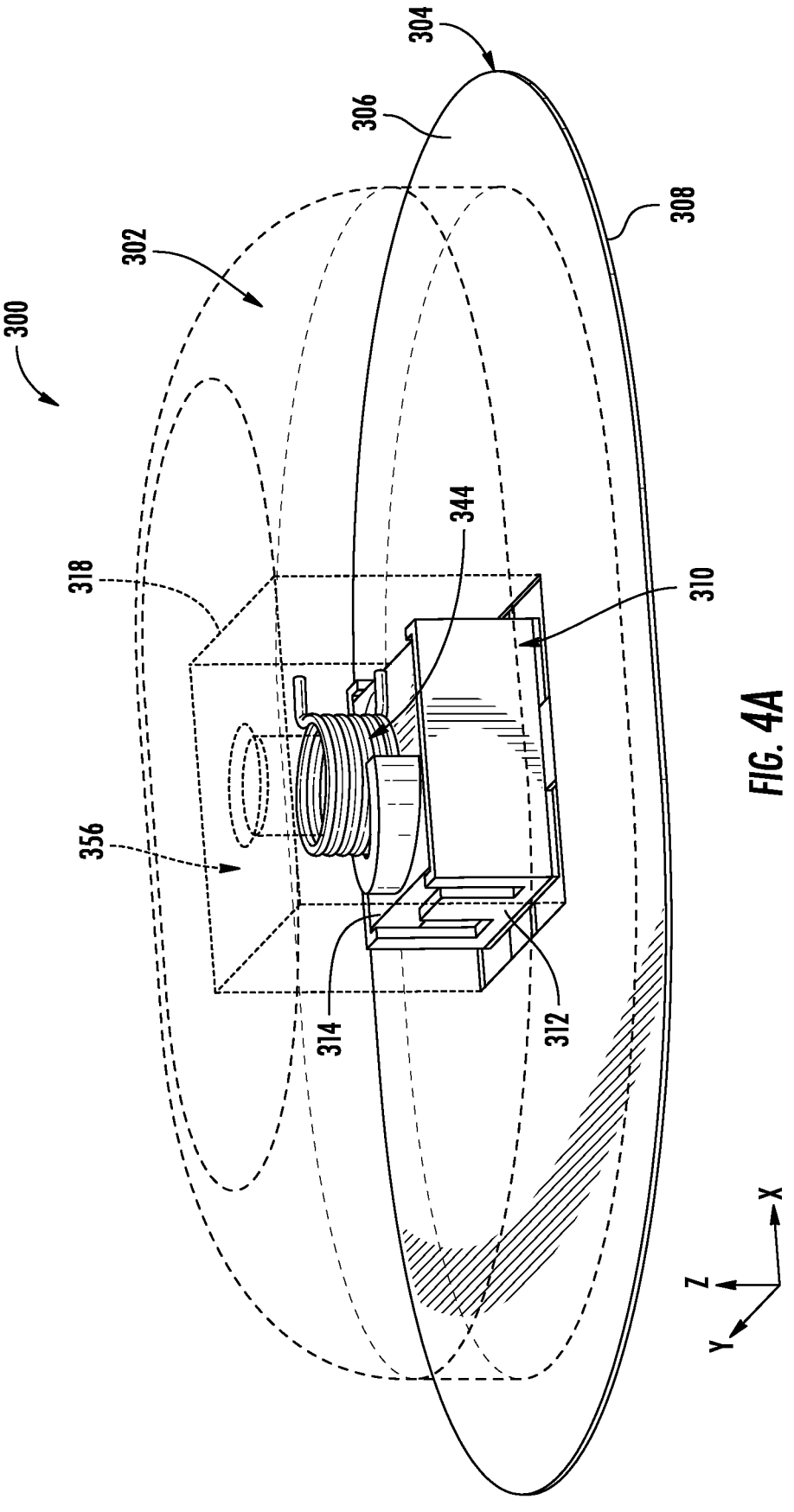
FIGS. 4A-4B are perspective views of a wearable drug delivery device according to embodiments of the present disclosure.
Figure 4B:
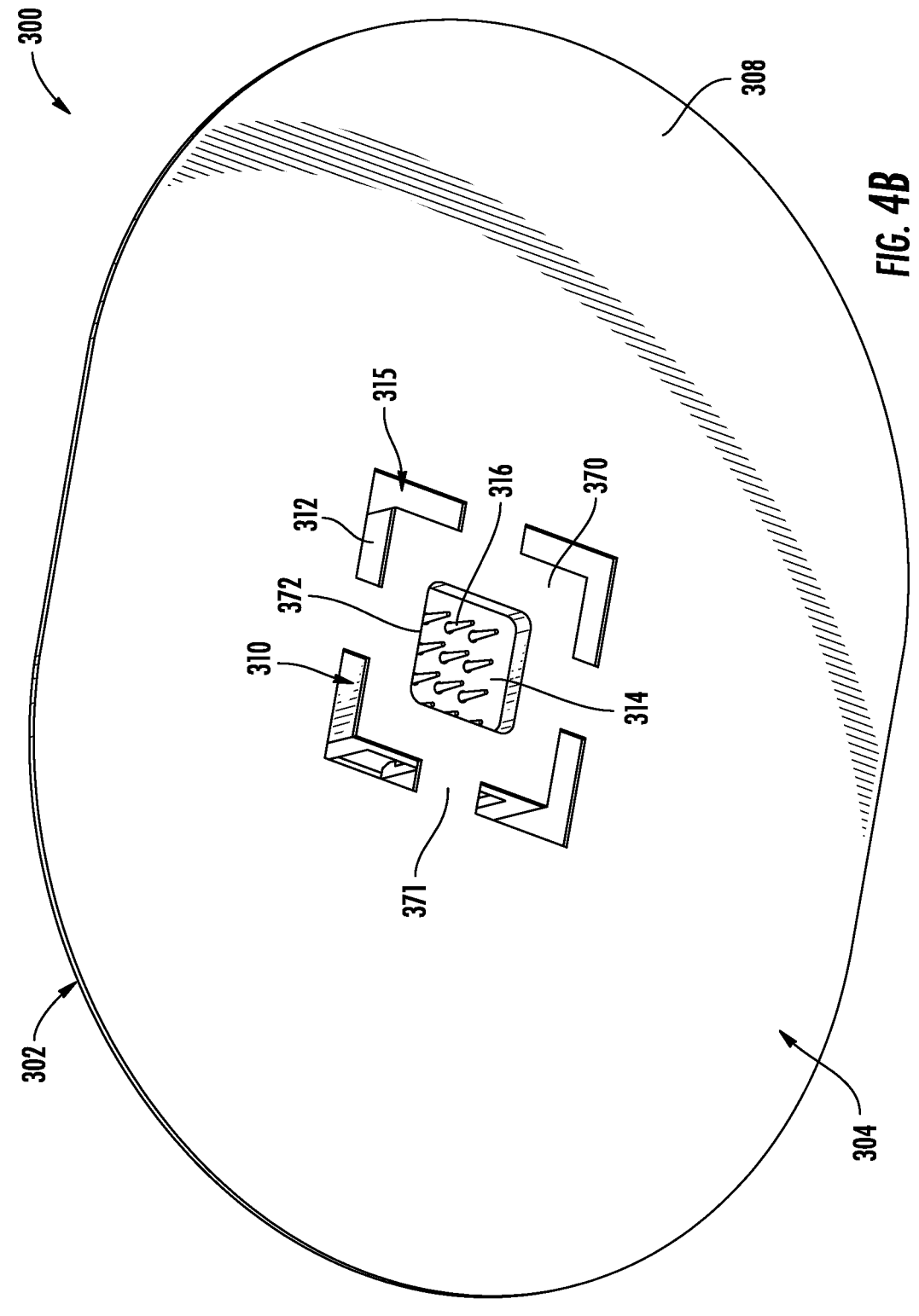
Figure 4C:
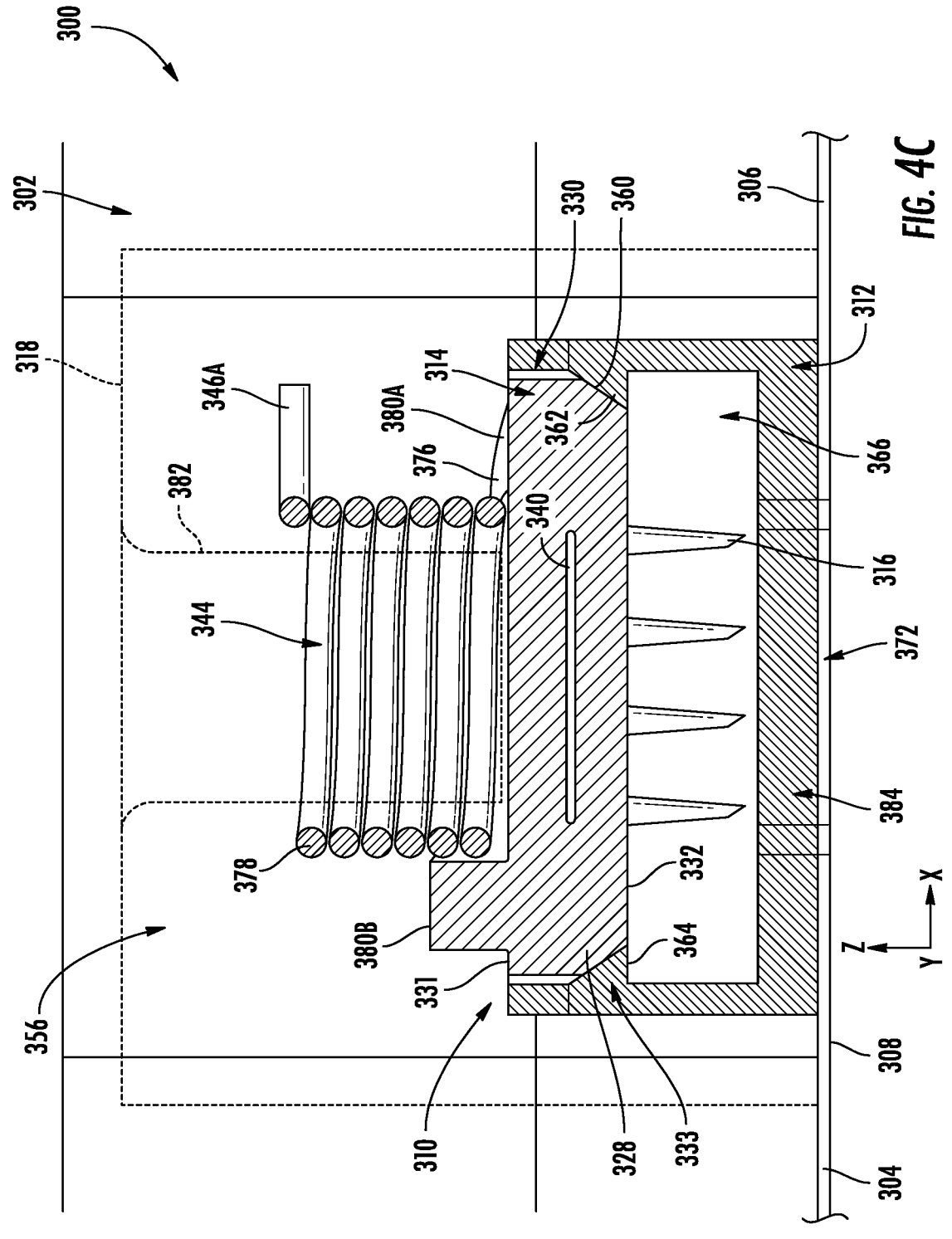
FIG. 4C is a side cross-sectional view of the wearable drug delivery device of FIGS. 4A-4B according to embodiments of the present disclosure.

FIGS. 4A-4C illustrate a portion of a device 300 according to embodiments of the present disclosure. As shown, the device 300 may include a pump housing 302 including a base 304 having an inner side 306 opposite an outer side 308, wherein the outer side 308 is directly attachable to the user. The device 300 may further include a microneedle assembly (hereinafter "assembly") 310 connected to the pump housing 302. In some embodiments, the assembly 310 may include a microneedle housing 312 and a carrier 314 positioned within the microneedle housing 312, wherein the carrier 314 includes a plurality of microneedles 316 (FIGS. 4B-4C) operable to penetrate the skin of the user to deliver a liquid drug to the user. The microneedle housing 312 and the carrier 314 may be located within a chamber 356 defined by a liquid barrier 318, which separates the assembly 310 from the other interior components (not shown) of the device 300. Although non-limiting, the liquid barrier 318 may be a polymer or silicon layer operable to provide a liquid tight seal around the assembly 310. In some embodiments, the liquid barrier 318 may be a portion of the pump housing 302. In some embodiments, the liquid barrier 318 may be coupled to the base 304. Although not shown, the assembly 310 may be coupled to a cannula (not shown) of the device 300. As will be described in greater detail below, the carrier 314 may be biased towards the skin of the user by a biasing device 344 (e.g., spring) operable to move the carrier 314 between a retraction position and an insertion position.

As best shown in FIG. 4B, the base 304 may include one or more openings 315 defining a central base 370, which is coupled to the microneedle housing 312. The central base 370 may be connected to base 304 by one or more connectors 371, wherein the openings 315 and the connectors 371 provide flexibility to a central portion of the device 300. As further shown, the central base 370 may include a central opening 372 proximate the microneedles 316. When the carrier 314 is biased towards the user, the microneedles 316 extend through the central opening 372 for engagement with the skin of the user.

As best shown in the side cross-sectional view of FIG. 4C, the carrier 314 may include a main body 328 initially positioned within an upper recess 330 of the microneedle housing 312. The main body 328 may include an inner surface 331 opposite an outer surface 332, wherein the microneedles 316 extend from the outer surface 332. The main body 328 may include a slot 340 fluidly connected with a cannula (not shown) and with one or more internal fluid conduits of each microneedle 316 for delivering the liquid drug into the dermal layer of the skin.

The main body 328 may further include a sloped side surface 360 engaged with a retention feature 333. In the non-limiting embodiment shown, the retention feature 333 may be a snap-fit tab having a first surface 362 operable to engage the sloped side surface 360 of the main body 328 when the carrier 314 is positioned within the upper recess 330, and a second surface 364 operable to engage or abut the inner surface 331 of the carrier 314 when the carrier 314 is positioned within a lower recess 366 of the microneedle housing 312. The corresponding angles of the first surface 362 and the sloped side surface 360 may initially prevent the carrier 314 from moving towards the user until a sufficient force causes the retention feature(s) 333 to deflect away from the carrier 314 (e.g., primarily along the x-axis). Once the carrier 314 moves between the upper recess 330 and the lower recess 366, engagement between the inner surface 331 of the carrier 314 and the second surface 364 of retention feature 333 prevents the carrier 314 from moving away from the user, e.g., along the z-axis.

The biasing device 344 may cause the carrier 314 to move from an initial position, as shown in FIG. 4C, to a final insertion position, in which the carrier 314 is engaged with the user. In the non-limiting embodiment shown, the biasing device 344 is a coil spring having a first tine 346A at a first end and a second tine 346B (FIG. 4A) at a second end, wherein the second tine 346B is in contact with the inner surface 331 of the carrier 314. More specifically, the second tine 346B of the coil spring may be positioned atop a sloped surface 376 of the carrier 314, wherein the sloped surface 376 wraps arounds a center portion 378 of the biasing device 344. As shown, the sloped surface 376 has a variable height (e.g., along the z-axis) between a first end 380A and a second end 380B. As the second tine 346B moves between the first and second ends 380A-380B of the sloped surface 376, the center portion 378 of the biasing device 344 is compressed until the carrier 314 is forced down into the lower recess 366, which in turn causes the microneedles 316 to extend through a housing opening 384 of the microneedle housing 312 and through the central opening 374 of the base 304. Once the microneedles 316 penetrate the skin of the user, an analyte level may be sampled and/or the liquid drug may be delivered through the cannula and the main body 328 of the carrier 314. After application of the carrier 314, the biasing device 344 and/or the retention feature(s) 333 may provide a sustained force on the microneedles 316 to further decrease the risk of the microneedles 316 coming out of the skin of the user.

Although not shown, in some embodiments, the device 300 may include an adhesive along the outer side 308 of the base 304 and/or along the outer surface 332 of the carrier 314. In various embodiments, any portion of the outer side 308 of the base 304 and any portion of the outer surface 332 of the carrier 314 can include an adhesive. The adhesives along the carrier 314 and the base 304 may be the same or different in various embodiments.

The carrier 314 is advantageously decoupled from the microneedle housing 312, allowing the carrier to "float" within the lower recess 366. As a result, minor upward forces (e.g., along the z-axis) on the base 304 will not transfer to the carrier 314 or the microneedles 316. Furthermore, due to the width (e.g., along the x-axis) of the lower recess 366 relative to the width of the carrier 314, lateral forces (e.g., along the x-axis and y-axis) are less likely to transfer to the carrier 314 or the microneedles 316.

Figure 5A:
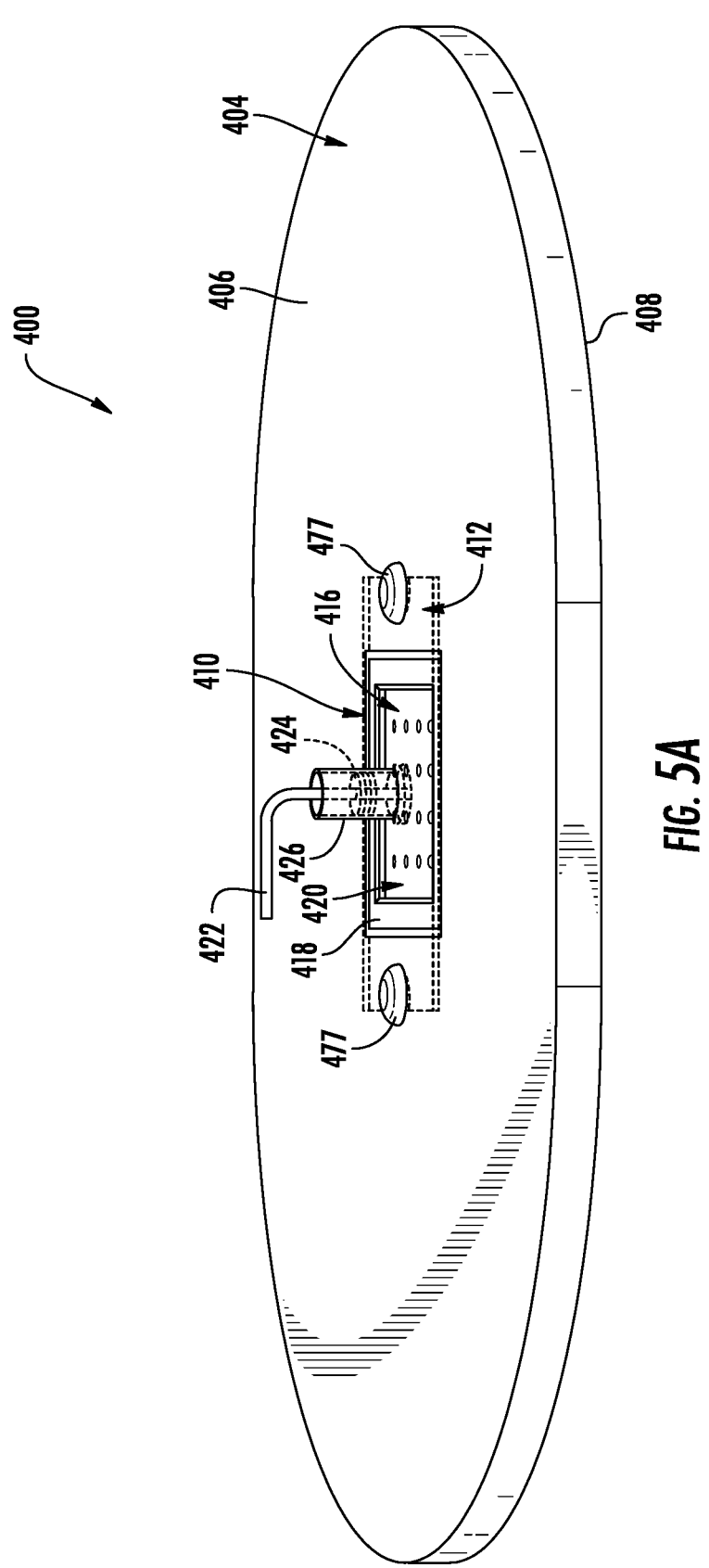
FIGS. 5A-5B are perspective views of a wearable drug delivery device according to embodiments of the present disclosure.
Figure 5B:
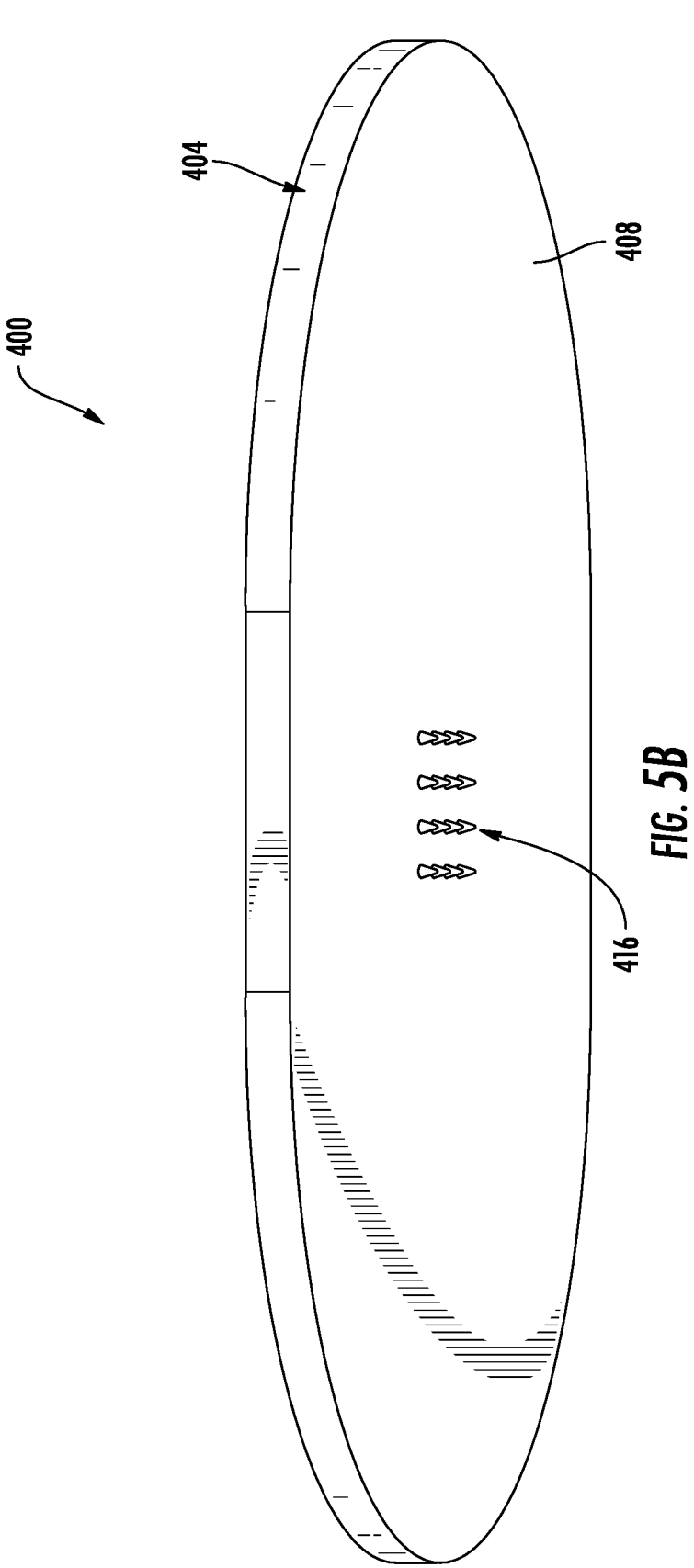
Figure 5C:
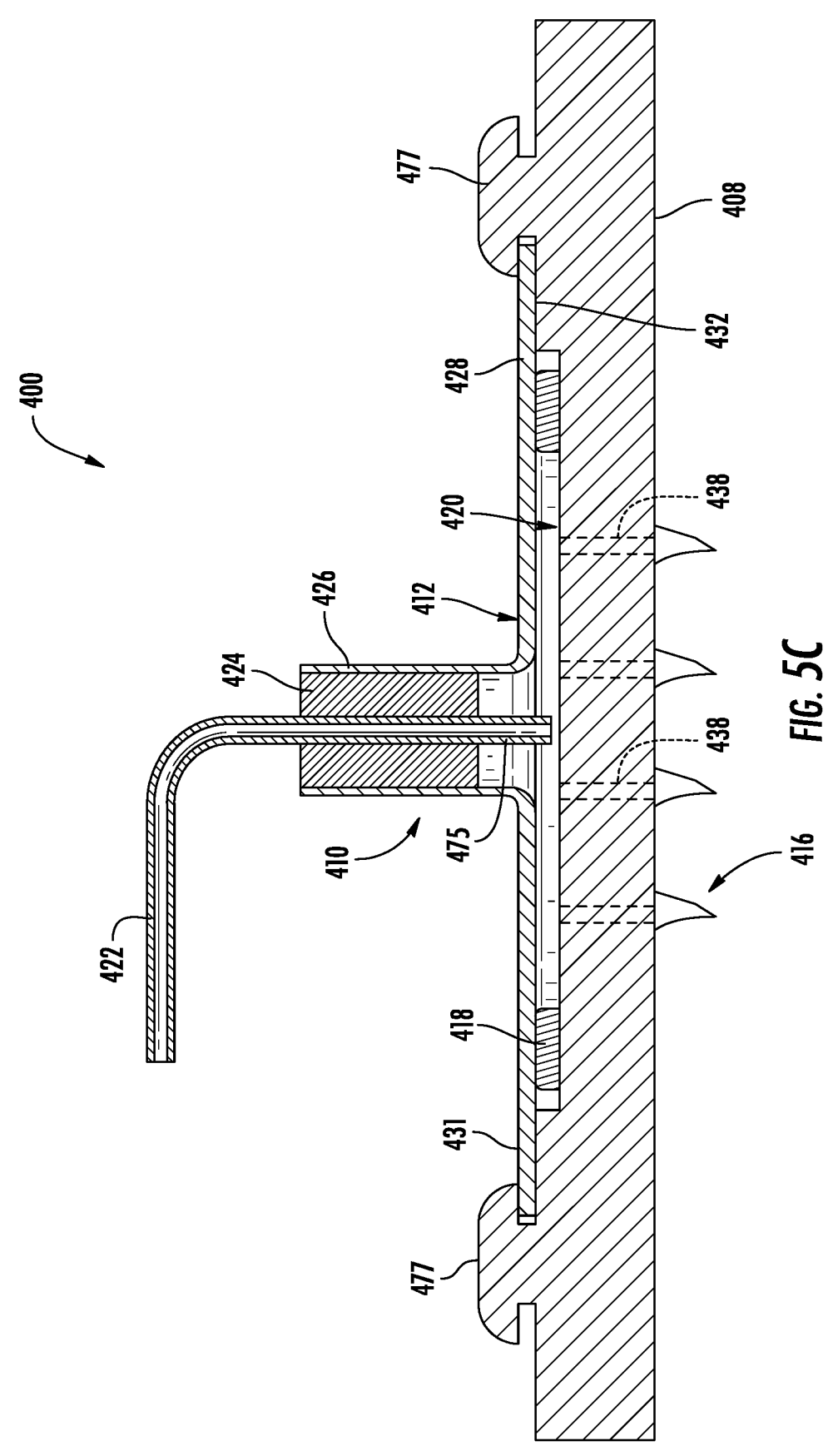
FIG. 5C is a side cross-sectional view of the wearable drug delivery device of FIGS. 5A-5B according to embodiments of the present disclosure.

FIGS. 5A-5C illustrate a portion of a device 400 according to embodiments of the present disclosure. As shown, the device 400 may include a base 404 including an inner side 406 opposite an outer side 408, wherein the outer side 408 is directly attachable to the user. Although not shown, in some embodiments, an adhesive is provided along a portion or all of the outer side 408 of the base 404.

The device 400 may further include a microneedle assembly (hereinafter "assembly") 410 connected to the base 404. In some embodiments, the assembly 410 may include a microneedle housing 412 and a plurality of microneedles 416 operable to penetrate the skin of the user to deliver a liquid drug to the user. The assembly 410 may further include a liquid barrier 418 positioned below microneedle housing 412, wherein the liquid barrier 418 and the microneedle housing 412 may define an internal chamber 420. Although non-limiting, the liquid barrier 418 may be a polymer or silicon layer operable to provide a liquid tight seal between the microneedle housing 412 and the base 404. In some embodiments, the microneedle housing 412 and the liquid barrier 418 may be secured to the base 404 by one or more fasteners 477.

The assembly 410 may be coupled to a cannula 422 of the device 400. In some embodiments, the cannula 422 may be secured to the microneedle housing 412 by an o-ring or plug 424 positioned within a neck 426 of the microneedle housing 412. The cannula 422 may terminate within the internal chamber 420 for delivering the liquid drug to the microneedles 416.

As best shown in FIG. 5B, the microneedles 416 may extend from the outer side 408 of the base 404. Although non-limiting, the microneedles 416 may be arranged as an array having any number of rows and columns. The microneedles 416 and/or the base 404 may be integrally manufactured out of a metal, polymer, or silicon. In various embodiments, the number and size of the microneedles 416 can be designed such that the collective cross sectional area of internal fluid conduits 438 (FIG. 5C) meets flow rate needs of a patient requiring the liquid drug.

As best shown in FIG. 5C, the microneedle housing 412 may include a main body 428 connected to the neck 426, wherein the main body 428 is positioned across the liquid barrier 418 and the internal chamber 420. The main body 428 may include an inner surface 431 opposite an outer surface 432, wherein the inner surface 431 may be engaged by the fasteners 477, which may be screws, bolts, tabs, clasps, or the like.

During operation, the base 404 may be pressed against the skin of the user, causing the microneedles 416 to penetrate the skin. The liquid drug may then be delivered through the cannula 422 and into the internal chamber 420. In some embodiments, a first end 475 of the cannula may terminate within the internal chamber 420. The internal chamber 420 may be fluidly connected with the internal fluid conduits 438 of the microneedles 416 for delivering the liquid drug from the cannula 422 to the dermal layer of the skin.

FIG. 6 illustrates an example process 500 according to embodiments of the present disclosure. At block 501, the process 500 may include providing a pump housing including a base attachable to a user. At block 502, the process 500 may include providing a carrier proximate an opening of the base, the carrier including a plurality of microneedles. In some embodiments, an adhesive may be provided along an outer side of at least one of: the base, and the carrier. In some embodiments, the adhesives along the base and carrier may be the same or different. In some embodiments, the microneedles may be arranged as an array having any number of rows and columns. In some embodiments, each of the microneedles may include an internal conduit for delivering a liquid drug to the user.

At block 503, the process 500 may include coupling a cannula to the carrier, the cannula operable to deliver the liquid drug to the user via the microneedles. In some embodiments, the cannula may be secured to the carrier by an o-ring or plug positioned within a neck of the carrier.

At block 504, the process 500 may include moving the carrier between a retracted position and an insertion position, wherein the plurality of microneedles penetrate a skin of the user when the carrier is in the insertion position. In some embodiments, moving the carrier between the retracted position and the insertion position comprises biasing the carrier using a biasing device coupled to the carrier.

In some embodiments, the biasing device is a spring. In some embodiments, an end of the spring is rotated along a sloped surface of the carrier to move the carrier towards the user. In some embodiments, a position of the carrier is maintained relative to the user using a retention feature of the microneedle housing.

In some embodiments, the process 500 may further include receiving the liquid drug into an internal chamber, wherein the cannula extends into the internal chamber, and delivering the liquid drug through the plurality of microneedles, wherein the internal chamber is fluidly connected with the plurality of microneedles. In some embodiments, the process 500 may further include sampling an analyte level in the patient, such as a blood glucose level, using the plurality of microneedles.

Figure 7:
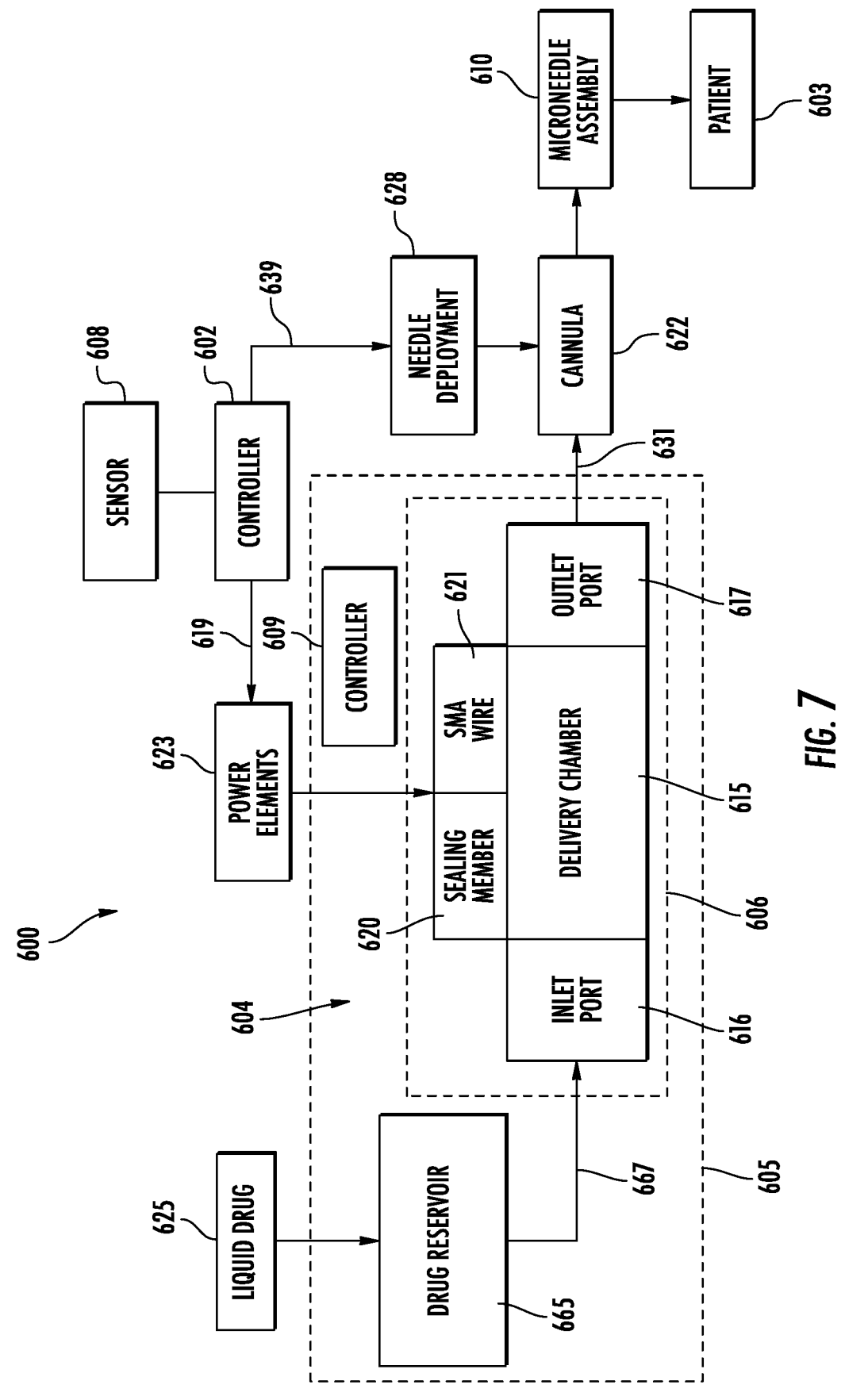
FIG. 7 illustrates a schematic diagram of a drug delivery system according to embodiments of the present disclosure.

FIG. 7 illustrates a simplified block diagram of an example system 600. The system 600 may be a wearable or on-body drug delivery device, such as the devices 100/200/300/400 described herein, attached to the skin of a user/patient 603. The system 600 may include a controller 602, a pumping mechanism 604 (hereinafter "pump 604"), and a sensor 608. The sensor 608 may be a glucose or other analyte monitor such as, for example, a continuous glucose monitor, and may be incorporated into the wearable device. The sensor 608 may, for example, be operable to measure blood glucose (BG) values of a user to generate a measured BG level signal 612. The controller 602, the pump 604, and the sensor 608 may be communicatively coupled to one another via a wired or wireless communication path. For example, each of the controller 602, the pump 604 and the sensor 608 may be equipped with a wireless radio frequency transceiver operable to communicate via one or more communication protocols, such as Bluetooth®, or the like. The system 600 may also include a delivery pump device (hereinafter "device") 605, which includes a drive mechanism 606. In some embodiments, the drive mechanism 606 may include the resilient sealing member 620 within a chamber 615, the resilient sealing member 620 connected to an SMA wire 621. The system 600 may include additional components not shown or described for the sake of brevity.

The controller 602 may receive a desired BG level signal, which may be a first signal, indicating a desired BG level or range for the patient 603. The desired BG level signal may be stored in memory of a controller 609 on device 605, received from a user interface to the controller 602, or another device, or by an algorithm within controller 609 (or controller 602) that automatically determines a BG level for the patient 603. The sensor 608 may be coupled to the patient 603 and operable to measure an approximate value of a BG level of the user. In response to the measured BG level or value, the sensor 608 may generate a signal indicating the measured BG value. As shown in the example, the controller 602 may also receive from the sensor 608 via a communication path, the measured BG level signal 612, which may be a second signal.

Based on the desired BG level signal and the measured BG level signal 612, the controller 602 or controller 609 may generate one or more control signals for directing operation of the pump 604. For example, one control signal 619 from the controller 602 or controller 609 may cause the pump 604 to turn on, or activate one or more power elements 623 operably connected with the device 605. The power elements 623 may activate the SMA wire 621, causing the SMA wire 621 to change shape and/or length, which in turn will change a configuration of the resilient sealing member 620. The specified amount of a liquid drug 625 (e.g., insulin, GLP-1, or a co-formulation of insulin and GLP-1; a chemotherapy drug; a blood thinner; or a pain medication) may then be drawn into the chamber 615, from a reservoir 665, via outlet conduit 667, and through an inlet port 616, in response to a change in pressure due to the change in configuration of the resilient sealing member 620. Ideally, the specified amount of the liquid drug 625 may be determined based on a difference between the desired BG level signal and the actual BG signal level 612. The specified amount of the liquid drug 625 may be determined as an appropriate amount of insulin to drive the measured BG level of the user to the desired BG level. Based on operation of the pump 604, as determined by the control signal 619, the patient 603 may receive the liquid drug from the reservoir 665. The system 600 may operate as a closed-loop system, an open-loop system, or as a hybrid system. In an exemplary closed-loop system, the controller 609 may direct operation of the device 605 without input from the controller 602, and may receive BG level signal 612 from the sensor 608. The sensor 608 may be housed within the device 605 or may be housed in a separate device and communicate wirelessly directly with the device 605.

As further shown, the system 600 may include a needle deployment component 628 in communication with the controller 602 or the controller 609. The needle deployment component 628 may include a needle/cannula 622 coupled to a microneedle assembly 610. The microneedle assembly 610 may be the same as any of the microneedle assemblies (e.g., 110, 210, 310, 410) described herein. The cannula 622 may form a portion of a fluid path coupling the patient 603 to the reservoir 665. More specifically, the inlet port 616 may be coupled to the reservoir 665 by the outlet conduit 667. The outlet conduit 667 may be of any size and shape and may be made from any material. The outlet conduit 667 can allow fluid, such as the liquid drug 625 in the reservoir 665, to be transferred to the device 605 through the inlet port 616.

The controller 602 or controller 609 may generate one or more control signals for directing operation of the microneedle assembly 610. For example, one control signal 639 from the controller 602 or controller 609 may cause a biasing device of the microneedle assembly 610 to activate, which causes a carrier of the microneedle assembly 610 to move from a retracted position to an insertion position. A plurality of microneedles of the microneedle assembly may penetrate the patient 603 to provide the liquid drug 625 to the patient when the carrier is in the insertion position.

The outlet port 617 may be coupled to the cannula 622 by a second fluid path component 631. The second fluid path component 631 may be of any size and shape and may be made from any material. The second fluid path component 631 may be connected to the cannula 622 to allow fluid expelled from the microneedle assembly 610 to be provided to the patient 603. The outlet conduit 667 and the second fluid path component 631 may be rigid or flexible.

The controller 602/609 may be implemented in hardware, software, or any combination thereof. The controller 602/609 may, for example, be a processor, a logic circuit or a microcontroller coupled to a memory. The controller 602/609 may maintain a date and time as well as other functions (e.g., calculations or the like) performed by processors. The controller 602/609 may be operable to execute an artificial pancreas (AP) algorithm stored in memory (not shown) that enables the controller 602/609 to direct operation of the pump 604. For example, the controller 602/609 may be operable to receive an input from the sensor 608, wherein the input indicates an automated insulin delivery (AID) application setting. Based on the AID application setting, the controller 602/609 may modify the behavior of the pump 604 and resulting amount of the liquid drug 625 to be delivered to the patient 603 via the device 605.

In some embodiments, the sensor 608 may be, for example, a continuous glucose monitor (CGM). The sensor 608 may be physically separate from the pump 604, or may be an integrated component within a same housing thereof. The sensor 608 may provide the controller 602 with data indicative of measured or detected blood glucose levels of the user.

The power element 623 may be a battery, a piezoelectric device, or the like, for supplying electrical power to the device 605. In other embodiments, the power element 623, or an additional power source (not shown), may also supply power to other components of the pump 604, such as the controller 602, memory, the sensor 608, and/or the needle deployment component 628.

In an example, the sensor 608 may be a device communicatively coupled to the controller 602 and may be operable to measure a blood glucose value at a predetermined time interval, such as approximately every 5 minutes, 10 minutes, or the like. The sensor 608 may provide a number of blood glucose measurement values to the AP application.

In some embodiments, the pump 604, when operating in a normal mode of operation, provides insulin stored in the reservoir 665 to the patient 603 based on information (e.g., blood glucose measurement values, target blood glucose values, insulin on board, prior insulin deliveries, time of day, day of the week, inputs from an inertial measurement unit, global positioning system-enabled devices, Wi-Fi-enabled devices, or the like) provided by the sensor 608 or other functional elements of the pump 604. For example, the pump 604 may contain analog and/or digital circuitry that may be implemented as the controller 602/609 for controlling the delivery of the drug or therapeutic agent. The circuitry used to implement the controller 602/609 may include discrete, specialized logic and/or components, an application-specific integrated circuit, a microcontroller or processor that executes software instructions, firmware, programming instructions or programming code enabling, for example, an AP application stored in memory, or any combination thereof. For example, the controller 602/609 may execute a control algorithm and other programming code that may make the controller 602/609 operable to cause the pump to deliver doses of the drug or therapeutic agent to a user at predetermined intervals or as needed to bring blood glucose measurement values to a target blood glucose value. The size and/or timing of the doses may be pre-programmed, for example, into the AP application by the patient 603 or by a third party (such as a health care provider, a parent or guardian, a manufacturer of the wearable drug delivery device, or the like) using a wired or wireless link.

Although not shown, in some embodiments, the sensor 608 may include a processor, memory, a sensing or measuring device, and a communication device. The memory may store an instance of an AP application as well as other programming code and be operable to store data related to the AP application.

In various embodiments, the sensing/measuring device of the sensor 608 may include one or more sensing elements, such as a blood glucose measurement element, a heart rate monitor, a blood oxygen sensor element, or the like. The sensor processor may include discrete, specialized logic and/or components, an application-specific integrated circuit, a microcontroller or processor that executes software instructions, firmware, programming instructions stored in memory, or any combination thereof.

As used herein, the algorithms or computer applications that manage blood glucose levels and insulin therapy may be referred to as an "artificial pancreas" algorithm-based system, or more generally, an artificial pancreas (AP) application. An AP application may be programming code stored in a memory device and that is executable by a processor, controller or computer device.

The techniques described herein for a drug delivery system (e.g., the system 600 or any components thereof) may be implemented in hardware, software, or any combination thereof. Any component as described herein may be implemented in hardware, software, or any combination thereof. For example, the system 600 or any components thereof may be implemented in hardware, software, or any combination thereof. Software related implementations of the techniques described herein may include, but are not limited to, firmware, application specific software, or any other type of computer readable instructions that may be executed by one or more processors. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

Some examples of the disclosed devices may be implemented, for example, using a storage medium, a computer-readable medium, or an article of manufacture which may store an instruction or a set of instructions that, if executed by a machine (i.e., processor or controller), may cause the machine to perform a method and/or operation in accordance with examples of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor when executing the programming code to perform functions, such as those described herein.

Certain examples of the present disclosed subject matter were described above. It is, however, expressly noted that the present disclosed subject matter is not limited to those examples, but rather the intention is that additions and modifications to what was expressly described herein are also included within the scope of the disclosed subject matter. Moreover, it is to be understood that the features of the various examples described herein were not mutually exclusive and may exist in various combinations and permutations, even if such combinations or permutations were not made express herein, without departing from the spirit and scope of the disclosed subject matter. In fact, variations, modifications, and other implementations of what was described herein will occur to those of ordinary skill in the art without departing from the spirit and the scope of the disclosed subject matter. As such, the disclosed subject matter is not to be defined only by the preceding illustrative description.

Program aspects of the technology may be thought of as "products" or "articles of manufacture" typically in the form of executable code and/or associated data that is carried on or embodied in a type of machine readable medium. Storage type media include any or all of the tangible memory of the computers, processors or the like, or associated modules thereof, such as various semiconductor memories, tape drives, disk drives and the like, which may provide non-transitory storage at any time for the software programming. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein," respectively. Moreover, the terms "first," "second," "third," and so forth, are used merely as labels and are not intended to impose numerical requirements on their objects.

The foregoing description of example examples has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner and may generally include any set of one or more limitations as variously disclosed or otherwise demonstrated herein.

What is claimed is:

1. A microneedle assembly of a wearable drug delivery device, the microneedle assembly comprising:
    a carrier coupled to a cannula;
    a microneedle housing surrounding the carrier and comprising a snap-fit tab operable to engage the carrier to maintain a position of the carrier relative to a user, wherein the microneedle housing and the carrier are decoupled from one another, wherein in a deployed configuration the microneedle housing constrains the carrier only in a direction away from the user and provides lateral clearance within a recess to reduce transfer of upward and lateral forces from the housing to the carrier; and a plurality of microneedles extending from the carrier, the plurality of microneedles operable to:

receive a liquid drug from the cannula; and penetrate a skin of the user to deliver the liquid drug to the user when the carrier is biased relative to the microneedle housing.

2. The microneedle assembly of claim 1, the carrier further comprising an internal chamber fluidly connected with the plurality of microneedles, wherein the cannula terminates within the internal chamber.

3. The microneedle assembly of claim 2, wherein each of the plurality of microneedles includes a fluid conduit for delivering the liquid drug from the internal chamber to the user.

4. The microneedle assembly of claim 2, the carrier further comprising an inner side opposite an outer side, wherein the plurality of microneedles extends from the outer side.

5. The microneedle assembly of claim 4, further comprising an adhesive along the outer side of the carrier.

6. The microneedle assembly of claim 1, further comprising a liquid barrier coupled to the carrier.

7. The wearable drug delivery device of claim 1, the microneedle assembly further comprising a biasing device coupled to the carrier, the biasing device operable to move the carrier between a retraction position and an insertion position.

* * * * *